United States Patent
Saitoh et al.

(10) Patent No.: US 10,232,187 B2
(45) Date of Patent: Mar. 19, 2019

(54) COIL DEVICE AND TRANSCRANIAL MAGNETIC STIMULATION SYSTEM

(71) Applicants: OSAKA UNIVERSITY, Suita-shi, Osaka (JP); The University of Tokyo, Tokyo (JP)

(72) Inventors: Youichi Saitoh, Ikeda (JP); Masaki Sekino, Tokyo (JP); Momoko Suyama, Nagasaki (JP); Keita Yamamoto, Tokyo (JP)

(73) Assignees: OSAKA UNIVERSITY, Osaka (JP); THE UNIVERSITY OF TOKYO, Tokyo (JP)

( * ) Notice: Subject to any disclaimer, the term of this patent is extended or adjusted under 35 U.S.C. 154(b) by 248 days.

(21) Appl. No.: 15/117,377

(22) PCT Filed: Feb. 13, 2015

(86) PCT No.: PCT/JP2015/054036
§ 371 (c)(1),
(2) Date: Aug. 8, 2016

(87) PCT Pub. No.: WO2015/122506
PCT Pub. Date: Aug. 20, 2015

(65) Prior Publication Data
US 2016/0346562 A1     Dec. 1, 2016

(30) Foreign Application Priority Data

Feb. 14, 2014 (JP) .................................. 2014-026955
Oct. 31, 2014 (JP) .................................. 2014-222650

(51) Int. Cl.
*A61N 5/10*        (2006.01)
*A61B 34/20*     (2016.01)
(Continued)

(52) U.S. Cl.
CPC ............... *A61N 2/02* (2013.01); *A61N 2/006* (2013.01)

(58) Field of Classification Search
CPC .................................. A61N 2/006; A61N 2/02
See application file for complete search history.

(56) References Cited

U.S. PATENT DOCUMENTS

2006/0094924 A1    5/2006   Riehl
2007/0027353 A1*   2/2007   Ghiron ..................... A61N 2/02
                                                            600/9

(Continued)

FOREIGN PATENT DOCUMENTS

JP     2012-125546 A     7/2012
JP     2013-046775 A     3/2013
(Continued)

OTHER PUBLICATIONS

International Search Report for PCT/JP2015/054036 dated May 19, 2015 [PCT/ISA/210].

(Continued)

*Primary Examiner* — Christine H Matthews
*Assistant Examiner* — Joshua Daryl D Lannu
(74) *Attorney, Agent, or Firm* — Sughrue Mion, PLLC

(57) ABSTRACT

A coil device for transcranial magnetic stimulation treatment, that generates an overcurrent uniformly across a wide range inside the head of a patient. The coil device includes a winding frame and a coil. A cylindrical surface of the winding frame has: an inner surface section arranged near the cranial surface during use; and an outer surface section forming a convex curved surface protruding towards the outside of the cylindrical surface, relative to a first direction parallel to a neutral axis and a second direction orthogonal to the first direction. The neutral axis draws a convex curve.

13 Claims, 20 Drawing Sheets

(51) Int. Cl.
  *A61N 2/02*   (2006.01)
  *A61N 2/00*   (2006.01)

(56) References Cited

U.S. PATENT DOCUMENTS

2010/0113959 A1* 5/2010 Pascual-Leone ...... A61N 2/006
                                                    600/544
2012/0157752 A1  6/2012 Nishikawa et al.

FOREIGN PATENT DOCUMENTS

| JP | 2013-078700 A   | 5/2013  |
|----|-----------------|---------|
| WO | 2006/050279 A2  | 5/2006  |
| WO | 2007/016279 A2  | 2/2007  |
| WO | 2010/147064 A1  | 12/2010 |

OTHER PUBLICATIONS

English Translation of International Preliminary Report on Patentability, dated Aug. 25, 2016, from the International Bureau in counterpart International application No. PCT/JP2015/054036.

* cited by examiner

CHANGES IN VALUES CORRESPONDING TO CHANGE IN VERTICAL LENGTH

CHANGES IN VALUES CORRESPONDING TO CHANGE IN NUMBER OF TURNS

EDDY CURRENT DISTRIBUTION OF FIGURE-EIGHT COIL

EDDY CURRENT DISTRIBUTION OF REFERENCE PARAMETER COIL

EDDY CURRENT DISTRIBUTION OF MOST EFFECTIVE COIL

MOST EFFECTIVE COIL

*Fig.17*
EDDY CURRENT DENSITY DISTRIBUTION (FIGURE-EIGHT COIL)
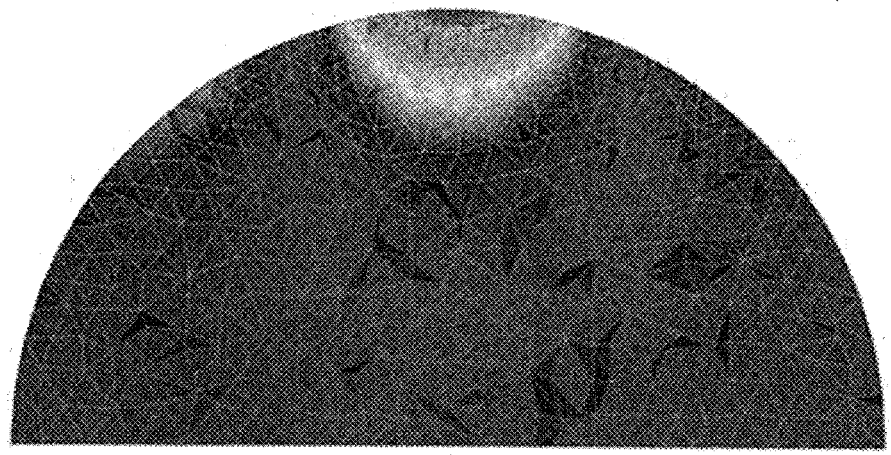
EDDY CURRENT DENSITY DISTRIBUTION (COIL OF FIG.16)
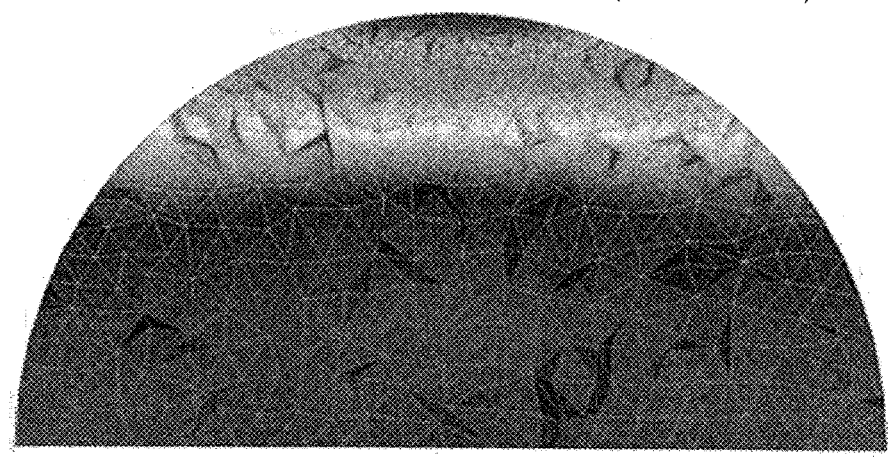
*Fig.18*
COIL MODEL WITH CONNECTION BETWEEN UPPER AND LOWER CIRCULAR ARCS
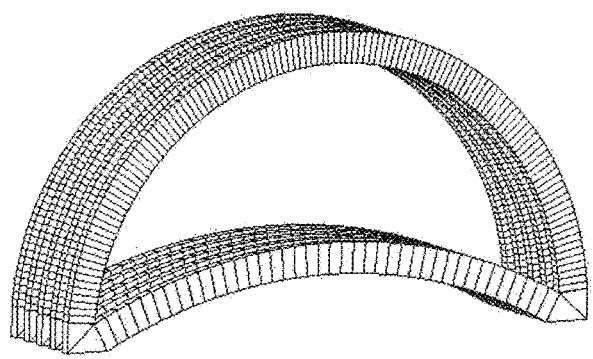

COIL MODEL WITHOUT CONNECTION BETWEEN UPPER AND LOWER CIRCULAR ARCS

DOME-TYPE COIL MODEL CREATED BASED ON SIMPLIFIED MODEL

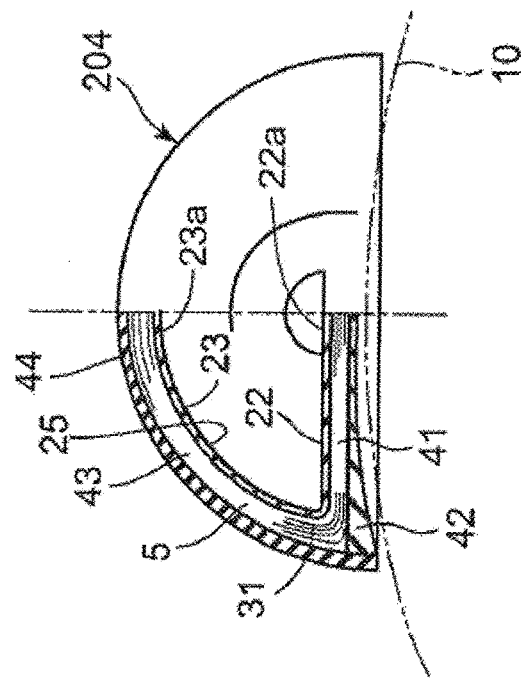
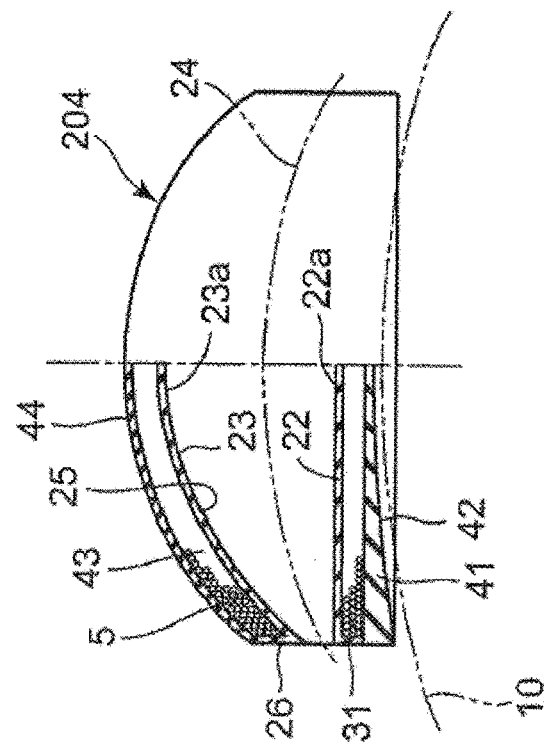

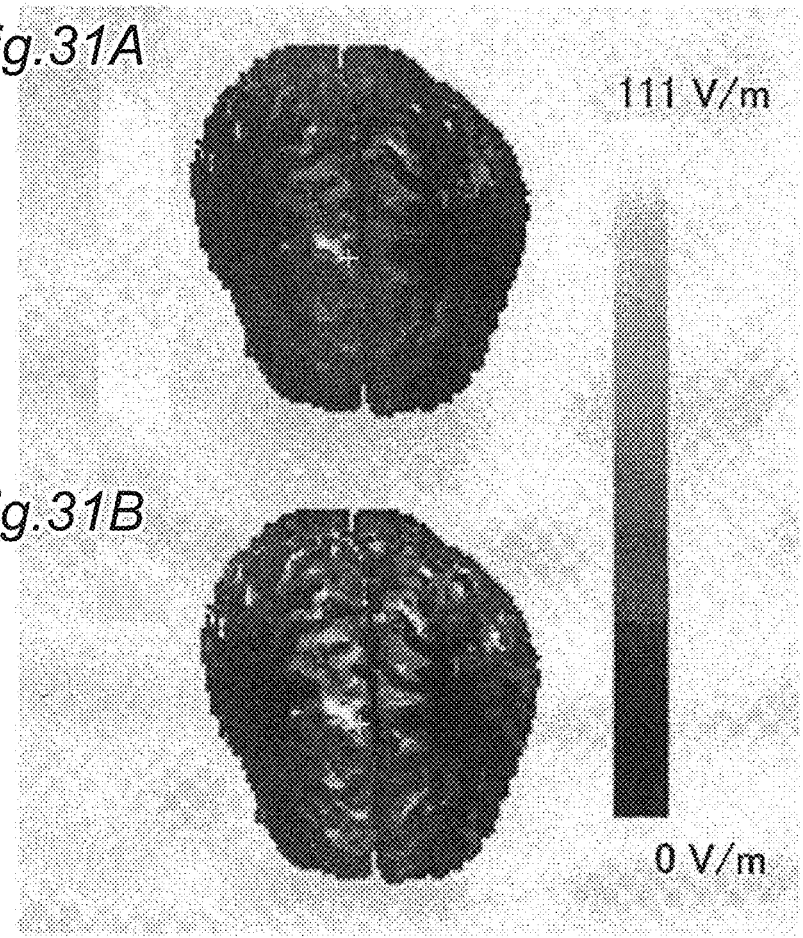

COIL DEVICE AND TRANSCRANIAL MAGNETIC STIMULATION SYSTEM

CROSS REFERENCE TO RELATED APPLICATIONS

This application is a National Stage of International Application No. PCT/JP2015/054036 filed Feb. 13, 2015, claiming priority based on Japanese Patent Application Nos. 2014-026955 filed Feb. 14, 2014 and 2014-222650 filed Oct. 31, 2014, the contents of all of which are incorporated herein by reference in their entirety.

TECHNICAL FIELD

The present invention relates to a coil device generating a magnetic field and a transcranial magnetic stimulation system using the coil device.

BACKGROUND ART

A transcranial magnetic stimulation is a technique of stimulating neurons by inducing an eddy current in the brain through electromagnetic induction. In this technique, as shown in FIGS. 1 and 2, an alternating-current or predetermined current waveform is applied to a stimulation coil placed on the skin of the head to form a variable magnetic field and to induce an eddy current in the direction opposite to the coil current in the brain under the effect of the variable magnetic field, and an action potential is generated by stimulating the neurons with the eddy current.

The transcranial magnetic stimulation is used in clinical examinations and neuroscience including measurement of nerve conduction velocity.

In recent years, magnetic stimulation is gathering attention as therapeutic application to neuropathic pain, Parkinson's disease, depression, etc. A drug therapy may not effective to these diseases in some cases and methods of treatment in such a case include applying an electrical stimulation to the brain by implanting an electrode into the brain. However, this method of treatment requires a craniotomy and is therefore often not desired by patients.

Thus, a repetitive transcranial magnetic stimulation performed by repeatedly applying a non-invasive magnetic stimulation not requiring a surgical operation is being studied as a method of treatment. For example, it is reported that a pain-relieving effect to intractable neuropathic pain is produced for about one day after magnetic stimulation to the primary motor cortex.

However, a conventional magnetic stimulation device weighs about 70 Kg and is available only in well-equipped medical institutions because electrical work is required for installation. Additionally, since a stimulation position is determined while referring to patient's MRI data during actual treatment, the treatment must be performed by a skilled health-care professional. In the treatment of intractable neuropathic pain, a coil must be positioned on the target primary motor cortex with accuracy of 1 mm.

PRIOR ART DOCUMENTS

Patent Documents

Patent Document 1: Japanese Laid-Open Patent Publication No. 2012-125546
Patent Document 2: International Publication No. 2010/147064

The present inventors have developed the magnetic stimulation device shown in FIG. 3 and have already made patent applications of an improved figure-eight type magnetic field generation coil and positioning (WO2010/147064, Japanese Laid-Open Patent Publication No. 2012-125546).

SUMMARY OF THE INVENTION

Problem to be Solved by the Invention

For transcranial magnetic stimulation therapy, various shapes of stimulation coils for magnetic stimulation methods are currently proposed, including a circular coil and a figure-eight coil shown in FIG. 4 as well as a four-leaf coil, a Hesed coil, and a coil having a multiplicity of small circular coils arranged on a head surface, and the circular coil and the figure-eight coil are currently mainly utilized.

The figure-eight coil has two circular coils arranged to partially overlap with each other and, when currents flow through the circular coils in opposite directions, the figure-eight coil can concentrate eddy currents immediately under a coil intersection part for localized stimulation.

On the other hand, a stimulation to a wider range may be effective rather than the localized stimulation depending on an object of treatment or a symptom of an individual patient.

Additionally, a coil with locally concentrated stimulation requires accurate positioning to an object site and, in this case, the accurate positioning must be performed by a navigation system etc.

For developing a magnetic stimulation used in a home treatment, a navigation system for determining a stimulation position by the hand of a non-healthcare professional is also under development. According to this system, a patient first wears eyeglasses with a magnetic sensor in a hospital, and calibration is performed by using a permanent magnet for wearing the eyeglasses at the same position every time. Subsequently, a medical doctor identifies an optimum stimulation position with a technique of combining an MR image with an optical tracking coordinate system and records data of the optimum stimulation position and random positions within a range of 5 cm around the optimum stimulation position. By recording the surrounding position data, the current position of the coil can visually be known when the patient determines the coil position. At the time of the home treatment, the calibration of the eyeglasses is first performed. Subsequently, a position of a permanent magnet mounted on a stimulation coil is three-dimensionally measured by comparing with the data. By visually confirming the current position of the coil and the optimum stimulation position, the coil can intuitionally be positioned. According to experiments, a guidance error of this navigation system is up to 5 mm from the optimum stimulation position and, on the other hand, the figure-eight coil described above can stimulate an intended site in a therapeutically effective manner when an irradiation site (the optimum stimulation position) is located within 5 mm. Therefore, if a treatment device applying a magnetic stimulation with the figure-eight coil is used at a stimulation position to which the coil is guided by using the navigation system, a site to be irradiated (the optimum stimulation position) may not fall within the stimulation effective range of the treatment coil, which makes it difficult to accurately stimulate a treatment portion. Therefore, it is necessary to develop a coil capable of generating an eddy current uniformly in a wider range such that an intended site can be stimulated in a therapeutically effective manner when a site to be irradiated is located within 10 mm, for example.

Thus, the present inventors propose a new dome-type coil device so as to achieve a stimulation coil with high robustness (i.e., capable of generating an eddy current uniformly in a wider range).

Means for Solving Problem

In the course of development of a coil device of the present invention, a simplified model and a conventional coil device were studied in terms of an eddy current density and a stimulation range. Additionally, based on this study results, a dome-typed coil device of the present invention was studied in terms of an eddy current density and a stimulation range.

The eddy current density was analyzed by the jω method based on the finite element method. A magnetic field Be is generated from the eddy current flowing inside the brain, and a vector potential Ae of the magnetic field is defined by Eq. 1 below.

[Eq. 1]

$$B_e = \nabla \times A_e \quad (1)$$

From the Ampere's law, Eq. 2 is satisfied between and an eddy current je and a magnetic field.

[Eq. 2]

$$\nabla \times \frac{B_e}{\mu_0} = j_e \quad (2)$$

In this equation, $\mu_0$ is a magnetic permeability of a vacuum. The following Ohm's law (Eq. 3) is satisfied between an eddy current and an electric field E.

[Eq. 3]

$$j_e = \sigma E \quad (3)$$

In this equation, σ is the electric conductivity of the brain. By substituting Eqs. 1, 3 into Eq. 2, Eq. 4 is acquired.

[Eq. 4]

$$\nabla \times \frac{1}{\mu_0} \nabla \times A_e = \sigma E \quad (4)$$

The vector potential Ae of the magnetic field generated by the eddy current and a vector potential Ac of a magnetic field generated by a coil are associated with an electric field by the Faraday's law as represented by Eq. 5.

[Eq. 5]

$$E = -\frac{\partial}{\partial t}(A_c + A_e) \quad (5)$$

When I is a coil current, r' is a position vector of windings of a coil, and r is a position vector for calculating a field, the vector potential of the magnetic field generated by the coil is calculated from the Biot-Savart's law as in Eq. 6.

[Eq. 6]

$$A_c = \frac{\mu_0 I}{4\pi} \int_C \frac{t(r')}{|r-r'|} dr' \quad (6)$$

By substituting Eq. 5 and Eq. 6 into Eq. 4, the following equation is acquired.

[Eq. 7]

$$\nabla \times \frac{1}{\mu_0} \nabla \times A_e = -\sigma \frac{\partial}{\partial t}\left(A_e + \frac{\mu_0 I}{4\pi} \int_C \frac{t(r')}{|r-r'|} dr'\right) \quad (7)$$

If an electromagnetic field temporally sinusoidally varies with an angular frequency ω, a complex field A*(x,y,z) can be defined by Eq. 8.

[Eq. 8]

$$A_e = Re(A^* \exp(j\omega t)) \quad (8)$$

By substituting Eq. 8 into Eq. 7 for complexification, an equation to be satisfied by the complex field is represented by Eq. 9.

[Eq. 9]

$$\nabla \times \frac{1}{\mu_0} \nabla \times A_e = -j\omega\sigma\left(A_e + \frac{\mu_0 I}{4\pi} \int_C \frac{t(r')}{|r-r'|} dr'\right) \quad (9)$$

In the analysis, this complex field was acquired as a result.

Based on a drive circuit developed by the present inventors, a capacitance of a capacitor was set to 180 μF and a pulse width was set to 298 μs, which was used when the figure-eight coil used for determining a reference parameter was connected. Setting of a voltage value was determined based on data of a current slew rate (a slope of a rising current (or an increase in the current per unit time) when the current corresponding to one cycle of a sine wave is applied to a coil so as to generate a magnetic field) reaching the stimulation threshold of the primary motor cortex acquired from six subjects (see Table 1).

TABLE 1

| Current Slew Rate Reaching Stimulation Threshold of Subjects | |
|---|---|
| Subjects | Current slew rate (A/μs) |
| A | 69 |
| B | 92 |
| C | 76 |
| D | 90 |
| E | 104 |
| F | 83 |
| Average | 85.7 |
| Standard variation | 12.4 |

From Table 1, it can be seen that the current slew rate of 110.5 A/μs (see Eq. 10) reaches the stimulation threshold in 97.7% of people.

[Eq. 10]

$$85.7 + 12.4 \times 2 = 110.5 \text{ A/μs} \quad (10)$$

Therefore, since the pulse width is 298 μs, an amplitude A=5.28 kA (see Eq. 11) was applied for analysis.

[Eq. 11]

$$\frac{2\pi A}{T} = 110.5 \text{ A/}\mu\text{s} \quad (11)$$

A hemispherical conductor of 200 mm in diameter was placed as a brain model at a position 1 cm away from the center of the coil. An electric conductivity was set to 0.1065 S/m equal to that of the grey matter at 3.36 kHz. For analysis related to the eddy current in the brain, the other biological tissues such as the cranium and an air layer were modeled as an insulation layer of 400 mm in diameter around the brain model. Since this air layer has a size resulting in sufficient attenuation of a magnetic field, it is considered that no distortion of the magnetic field occurs in the vicinity of the coil. In the whole model, the number of contact points was about 20000, the number of elements was about 100000.

In this analysis, evaluation objects were an eddy current density, a spread of a current density in directions parallel and perpendicular to a coil conductive wire, and a coil inductance. For the eddy current density, a value immediately under the coil center considered as a maximum value was used. For the spread of the current density, a width is used that corresponds to a half of a current density maximum value on a brain model surface as shown in FIG. 5. The coil inductance was used only in an air region for the analysis and is obtained from Eq. 12 by using the sum of magnetic field energy in the air region.

[Eq. 12]

$$\frac{1}{2}LI^2 = \frac{1}{2\mu}\int B^2 \, dV \quad (12)$$

Since a pulse width T considered effective for producing a therapeutic effect is about 200 to 300 µs, when C=180 µF is substituted into Eq. 13, it is considered that the inductance of 5.63 µH to 12.6 µH is desirable in terms of magnetic stimulation.

[Eq. 13]

$$T = 2\pi\sqrt{LC} \quad (13)$$

In this study, a dome-type coil shown in FIG. 6 is proposed as a coil with high robustness against a positioning error and a coil capable of magnetically stimulating a wider range. It is considered that this dome-type coil can maintain a level of eddy current density and widen a range in which an eddy current flows with high density while having changes in cross sections to make the inductance smaller. To evaluate this dome-type coil, a simplified model shown in FIG. 7 was used.

For this simplified model, which is based on design parameters of a figure-eight coil shown in FIG. 8 experimentally produced by the present inventors, a conductor of 6 mm in width and 2 mm in height was used, and reference parameters were determined by setting a conductor interval to 5 mm equal to that of the figure-eight coil to achieve the coil width of 97 mm, a horizontal length to 112 mm equal to the diameter of the figure-eight coil, a vertical length to 27 mm so that the rectangular cross-sectional area of the simplified model becomes equal to the cross-sectional area of the circle having the diameter equal to a half of the outer diameter of the figure-eight coil, and the number turns to 20 equal to that of the figure-eight coil. These reference parameters were each independently changed to achieve a coil width from 49.55 mm to 154 mm, a horizontal length from 52 mm to 175 mm, a vertical length from 15 mm to 39 mm, the number or turns from 10 to 30. When the number or turns was changed, the coil width was kept constant and the conductor interval was changed in accordance with the number of turns.

FIGS. 9 to 12 show results when the parameters were changed. Shaded frames in FIGS. 9 to 12 indicate a range of inductance from 5.63 µH to 12.6 µH considered desirable. As the coil width becomes larger, the eddy current spread becomes larger and the inductance becomes smaller. However, on the other hand, the current density drastically becomes smaller. When the size in the horizontal direction is changed, the eddy current spread is less changed while the inductance significantly varies, and the eddy current density becomes larger in accordance with an increase in the horizontal direction. A change in size in the vertical direction has almost no effect on the eddy current spread and has an effect only on the current density, and the current density becomes larger when the vertical size is larger.

Although the number of turns has almost no effect on the eddy current spread, it was found that the eddy current density becomes larger as the number of turns increases. In the results of analysis of the conventional figure-eight coil under the same conditions, the eddy current density was 24.32 A/m$^2$, the eddy current spread was 4.29 cm×7.55 cm, and the inductance was 9.71 µH.

In the results of the eddy current density analysis with the simplified coil, the coil design with the maximum vertical conductive wire length of 39 mm was most effective because of the eddy current density of 8.02 A/m$^2$, the eddy current spread of 6.61 cm×12.1 cm, and the inductance of 12.67 µH.

FIGS. 13 to 15 show the eddy current distributions of the figure-eight coil, the coil set to the reference parameters, and the most effective coil. Although the maximum eddy current density is inferior to the figure-eight coil, the coil enabled the generation of the eddy current in a wider range, which is the object of this study.

The coil width has a large effect on the eddy current spread, and the eddy current spread becomes larger in accordance with the coil width, while the eddy current density drastically becomes smaller. This is considered because an increase in the conductor interval causes magnetic fluxes to leak between conductive wires, which makes a change in magnetic fluxes passing through a living body smaller. On the other hand, although the three parameters of the horizontal length, the vertical length, and the number of turns of the conductive wire cause no substantial change in the eddy current spread, the eddy current density becomes larger as the inductance becomes larger. Changes in maximum current density per inductance will be compared. A change in the horizontal length corresponds to 1 µH:0.46 A/m$^2$, the vertical length corresponds to 1 µH:0.80 A/m$^2$, and a change in the number of turns corresponds to 1 µH:0.68 A/m$^2$ From the above, it can be seen that the vertical length has a larger effect on the maximum current density. This is considered because an increase in vertical length makes a distance larger between the brain and the conductive wire through which the current flows in the direction opposite to that of the conductive wire generating the induced current, and makes the effect thereof smaller.

From the above, it is considered that the dome-type coil is effectively designed by changing the coil width so as to increase the eddy current spread while compensating the reduction in the eddy current density due to the increase by mainly changing the vertical length of the conductive wire. FIG. 17 shows analysis results of the figure-eight coil and the most effective coil of FIG. 16 as cross-sectional views in terms of eddy current density distributions inside conductors. From these results, it can be seen that the dome-type coil can generate an eddy current deeper in a wider range as compared to the figure-eight coil.

Based on the analysis results from the simplified model, a dome-type coil was modeled. In modelling of the dome-type coil shown in FIG. 6, the time required for the modeling can significantly be reduced by using a model without connection between upper and lower circular arcs as shown in FIG. 19. Therefore, results of analysis under the same analysis conditions will be compared between a model with connection between upper and lower circular arcs as shown in FIG. 18 and the model without connection between upper and lower circular arcs as shown in FIG. 19. The coils used were four-turn models having the horizontal length of 117 mm, the width of upper and lower conductive wires of 34 mm, and the conductive wire interval of 3 mm.

The analysis results are described in Table 2. From these results, it was revealed that the both models have no significant difference. From the above, the coil model without connection between upper and lower circular arcs was used for the modeling of the dome-type coil.

TABLE 2

Comparison of Analysis Results Based on Whether Upper and Lower Conductive Wires Are Connected

|  | Model with connection between wires | Model without connection between wires |
|---|---|---|
| Maximum eddy current density | 6.662 A/m$^2$ | 6.636 A/m$^2$ |
| Range of eddy current density | 3.16 × 9.23 cm | 3.16 × 8.73 cm |
| Inductance | 1.90 μH | 1.79 μH |

Based on the model of FIG. 16 determined as the most effective coil in the analysis with the simplified model, a 20-turn dome-type coil was modeled to have the horizontal length of 112 mm, the vertical length of 39 mm, and the coil width of 97 mm as shown in FIG. 20, and was analyzed under the same analysis conditions.

Table 3 shows comparison between the analysis results of the coil of FIG. 16 determined as being most effective with the simplified model and the analysis results of the dome-type coil of FIG. 20. From these results, it is expected that since forming into a dome shape considerably reduces the inductance although the maximum eddy current density becomes smaller, the maximum eddy current density can be set to the same value as that of the simplified coil by further changing the parameters at the time of production of the dome-type coil so as to make the inductance larger. From the distribution of the eddy current viewed from the coil side shown in FIGS. 21A and 21B, it can be seen that the anisotropy is reduced in the spread of the eddy current distribution as compared to the simplified coil and that the eddy current can more uniformly be generated in a wide range.

TABLE 3

Comparison of Analysis Results between Simplified Coil and Dome-Type Coil

|  | Simplified Coil | Dome-type Coil |
|---|---|---|
| Maximum eddy current density | 8.02 A/m$^2$ | 6.75 A/m$^2$ |
| Range of eddy current density | 6.61 × 12.1 cm | 7.30 × 10.2 cm |
| Inductance | 12.67 μH | 6.52 μH |

From the analysis result of the dome-type coil model, it was found that the inductance is significantly suppressed by making a change in radius of the upper circular arc. This matches the initial assumption of "inducing the eddy current uniformly in a wide range while suppressing the inductance" made in the proposition of the dome-type coil. When this dome-type coil is produced, both upper and lower conductive wires are made to have the same curvature in two horizontal directions. Based on this premise, it can be understood that the parameters are narrowed down to three parameters of "the number of turns, the vertical length, and the upper conductive wire curvature."

The present invention proposes the dome-type coil as a new stimulation coil with high robustness against a positioning error, and the simplified model thereof was used in the analysis of the eddy current density, the eddy current spread, and the inductance according to changes in parameters. Based on the results from the simplified model, the dome-type coil model was produced and the analysis results were compared. As a result, it was found that the coil designed in this way can induce the eddy current in a wider range as compared to the figure-eight coil and that forming into a dome shape can suppress the inductance while maintaining the induction of the eddy current in the wider range.

The present invention was conceived based on the knowledge described above and provides a coil device used in a transcranial magnetic stimulation treatment placed on a head surface to stimulate neurons by generating an electric current in the brain through electromagnetic induction and a transcranial magnetic stimulation system having this coil device, the coil device comprising a spool having a neutral axis acquired by connecting centers of gravity in transverse cross sections and a tubular surface surrounding the neutral axis; and a coil made up of a conductive wire wound on the tubular surface around the neutral axis, the tubular surface having an inner surface portion located close to the head surface during use, and an outer surface portion forming a convex curved surface protruding outward of the tubular surface with respect to a first direction parallel to the neutral axis and a second direction orthogonal to the first direction, the neutral axis forming a convex curve protruding from the inner surface portion toward the outer surface portion.

The coil device of the present invention configured as described above is disposed such that the inner surface portion of the coil device faces the patient's head surface during use. In this state, when an alternating-current or another predetermined current waveform is applied to the coil, a magnetic field is formed inside the coil. This magnetic field extends along the neutral axis of the spool and deflects from the center of the spool toward the end parts of the spool to come gradually closer to the patient's head in accordance with the shape of the spool before being emitted from the end parts of the coil. The emitted magnetic field advances toward the patient's head and generates an eddy current uniformly in a wide range in the patient's head. Therefore, even when the position of the coil device somewhat deviates from an intended position, the eddy current can certainly be generated in the target site.

Additionally, since a stimulation to a wider range may be effective rather than the localized stimulation depending on an object of treatment or a symptom of an individual patient, a treatment coil adapted to such a treatment can be achieved.

In another form of the present invention, the inner surface portion is a curved surface recessed in a concave shape toward the inside of the tubular surface. According to this coil device, the coil device can disposed substantially exactly along the patient's head surface and, therefore, the positioning accuracy of the coil device is further improved, and the magnetic field emitted from the coil can efficiently be collected to the patient's head.

In another form of the present invention, the inner surface portion is a flat surface. In this case, preferably, the coil device is provided with an inner housing portion covering a coil portion located on the inner surface portion, and the inner housing portion has an outer surface that is a curved surface recessed in a concave shape toward the inside of the tubular surface.

In another form of the present invention, the tubular surface has end-part transverse cross sections on one end side and the other end side of the neutral axis smaller than a center-part transverse cross section located at a center between the one end side and the other end side. In this form, preferably, the transverse cross sections of the tubular surface are configured to become gradually smaller from the center-part transverse cross section toward the end-part transverse cross sections.

In the above forms, preferably, the neutral axis is an axis passing through centroids or centers of gravity of the transverse cross sections of the tubular surface. As a result, the magnetic field of the coil deflects from the center of the spool toward the end parts of the spool to come gradually closer to the patient's head before being emitted from the end parts of the coil, and generates an eddy current uniformly in a wide range in the patient's head.

The spool may be either a hollow member or a solid member extending along the neutral axis.

BRIEF DESCRIPTION OF DRAWINGS

FIG. 17 is a diagram of eddy current density distributions when the figure-eight coil and the coil of FIG. 16 are used.

FIG. 18 is a diagram of a coil model with connection between upper and lower circular arcs.

FIG. 27A is a longitudinal cross-sectional view of a coil unit of a third embodiment.

FIG. 27B is a transverse cross-sectional view of the coil unit of the third embodiment.

FIGS. 31A and 31B are diagrams of induced electric field distributions of the dome-type coil of the present invention when a numerical brain model is used.

MODES FOR CARRYING OUT THE INVENTION

Figure 1:
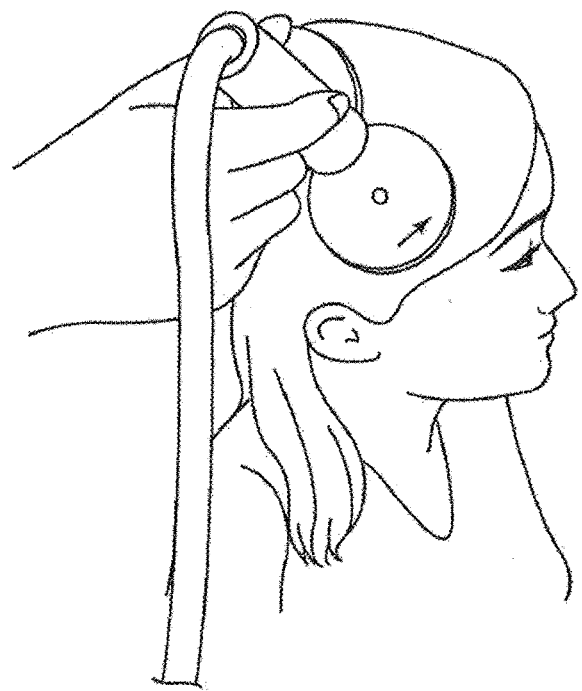
FIG. 1 is a diagram of a state of providing a magnetic stimulation treatment to a patient.
Figure 2:
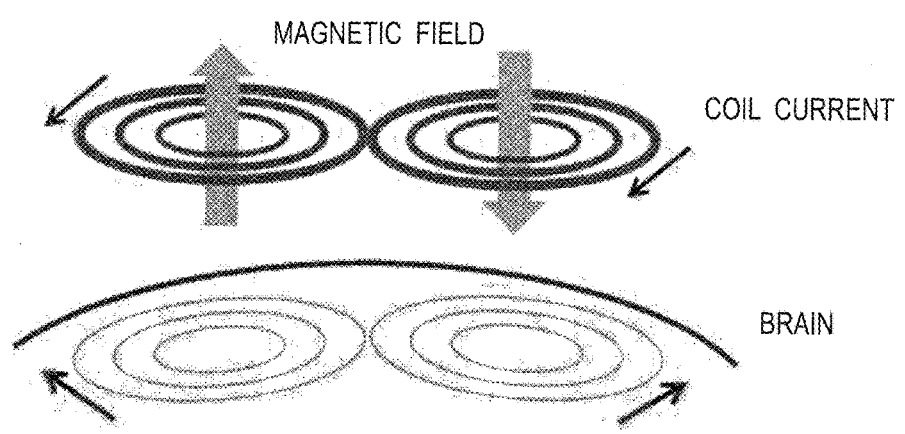
FIG. 2 is a diagram of an eddy current induced by a figure-eight coil.
Figure 3:
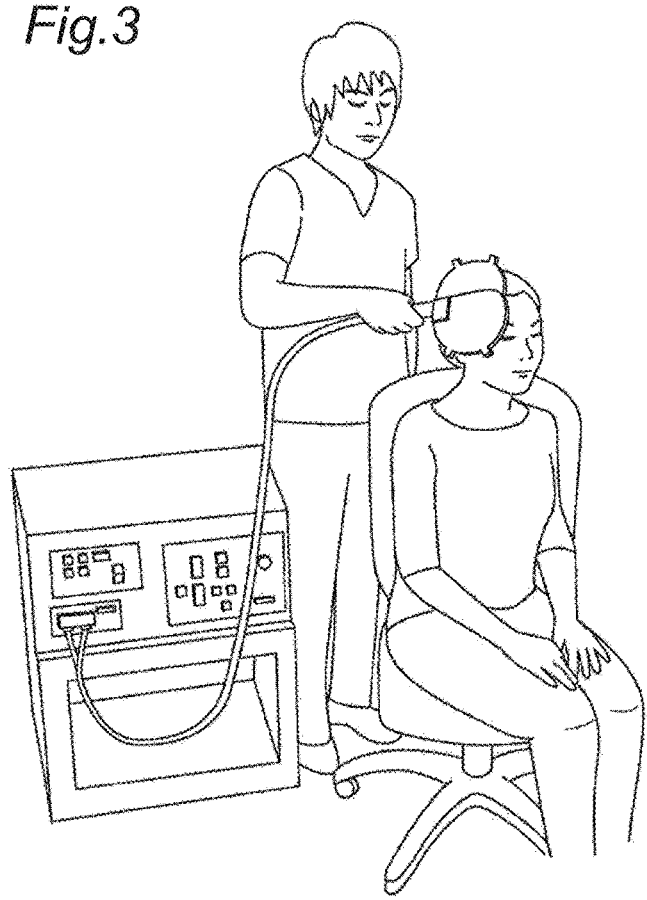
FIG. 3 is a diagram of a usage state of a magnetic stimulation device for home treatment.
Figure 4:
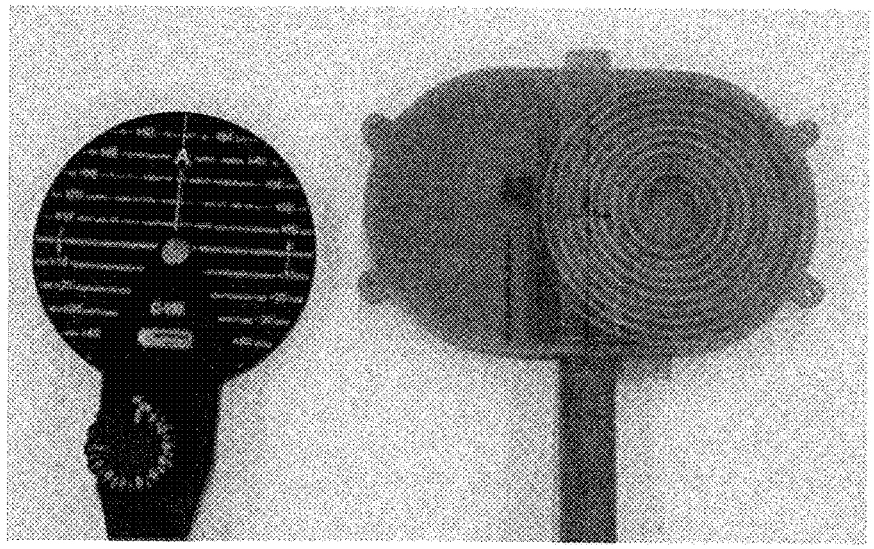
FIG. 4 is a diagram of a circular coil (left) and a figure-eight coil (right).
Figure 5:
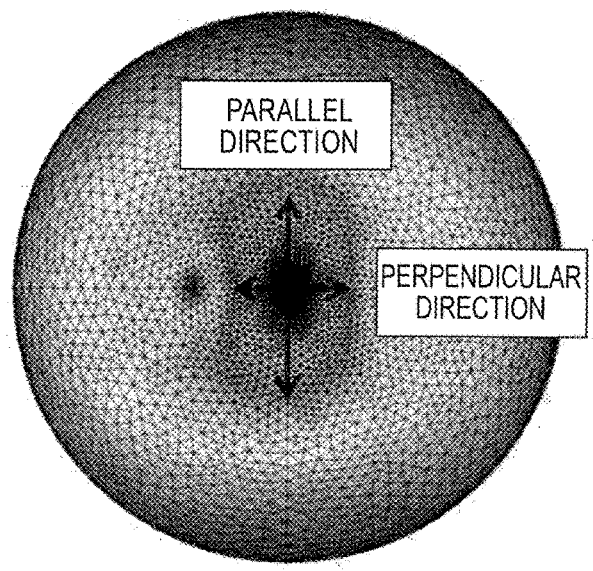
FIG. 5 is a diagram of directions of evaluation of a spread of current density.
Figure 6:
FIG. 6 is a diagram of a coil model used for a coil device according to the present invention.
Figure 7:
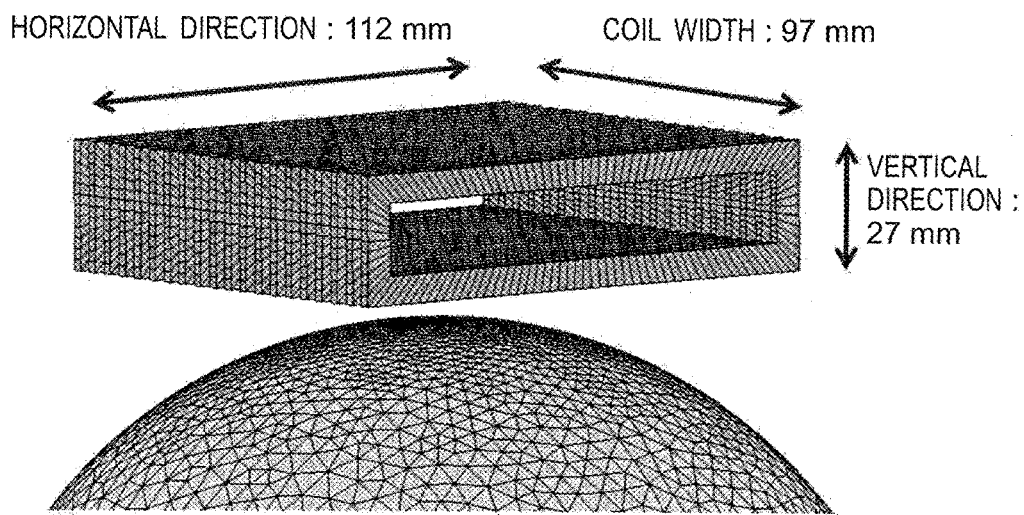
FIG. 7 is a diagram of a simplified model utilized for analysis.
Figure 8:
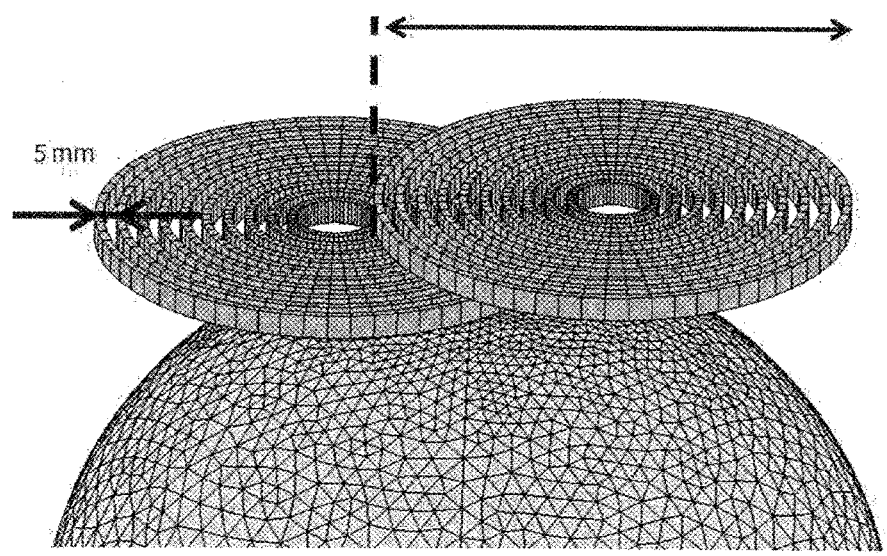
FIG. 8 is a schematic of a figure-eight coil.
Figure 9:
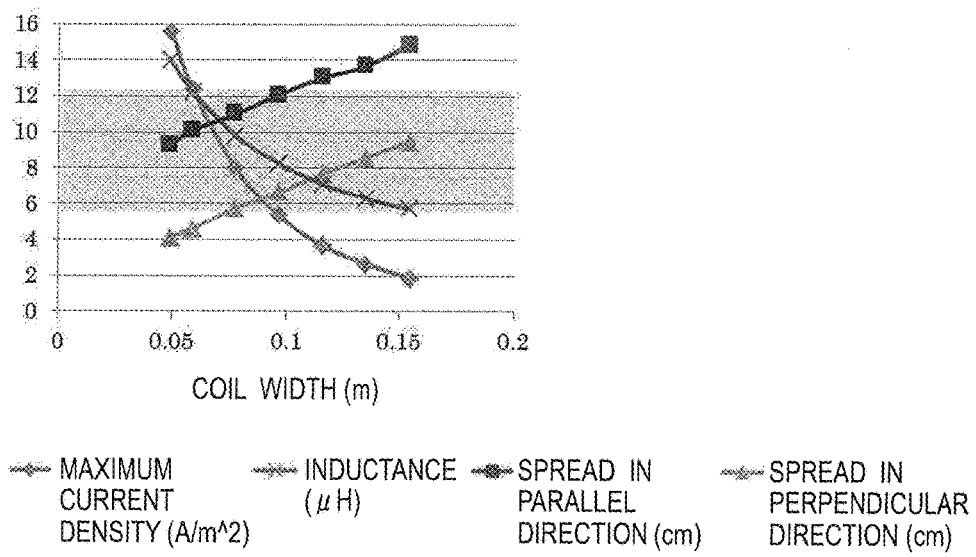
FIG. 9 is a graph of a relationship between a coil width and a maximum current density/an inductance/a spread of the magnetic field in parallel direction/a spread of the magnetic field in perpendicular direction.
Figure 10:
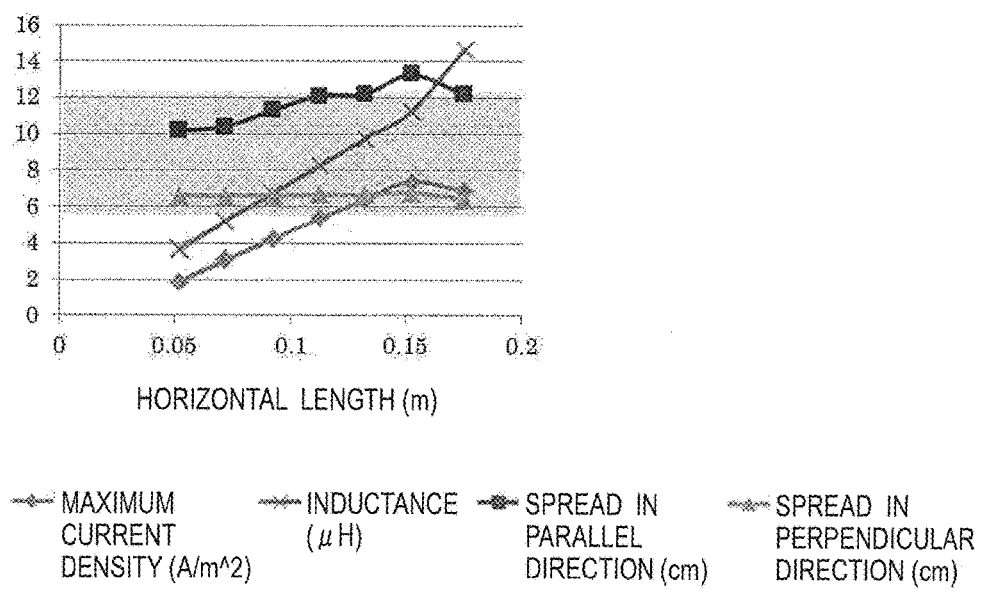
FIG. 10 is a graph of a relationship between a horizontal length and a maximum current density/an inductance/a spread of the magnetic field in parallel direction/a spread of the magnetic field in perpendicular direction.
Figure 11:
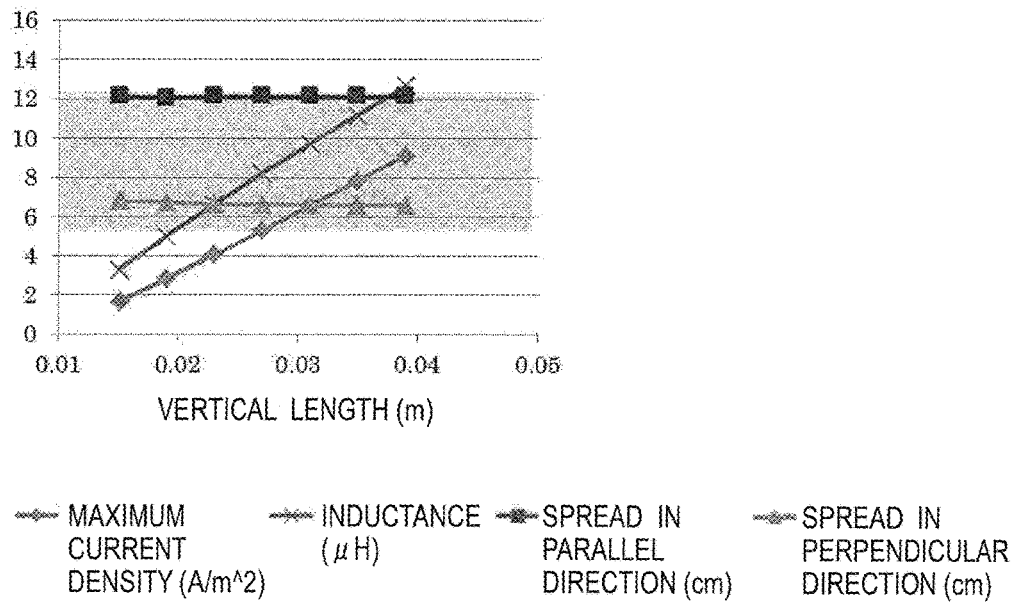
FIG. 11 is a graph of a relationship between a vertical length and a maximum current density/an inductance/a spread of the magnetic field in parallel direction/a spread of the magnetic field in perpendicular direction.
Figure 12:
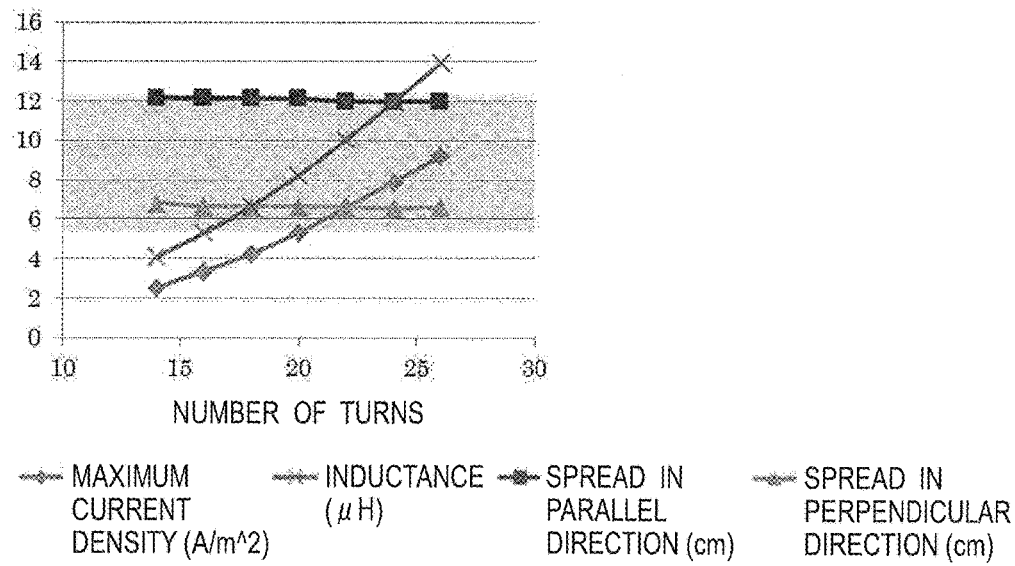
FIG. 12 is a graph of a relationship between the number of turns and a maximum current density/an inductance/a spread of the magnetic field in parallel direction/a spread of the magnetic field in perpendicular direction.
Figure 13:
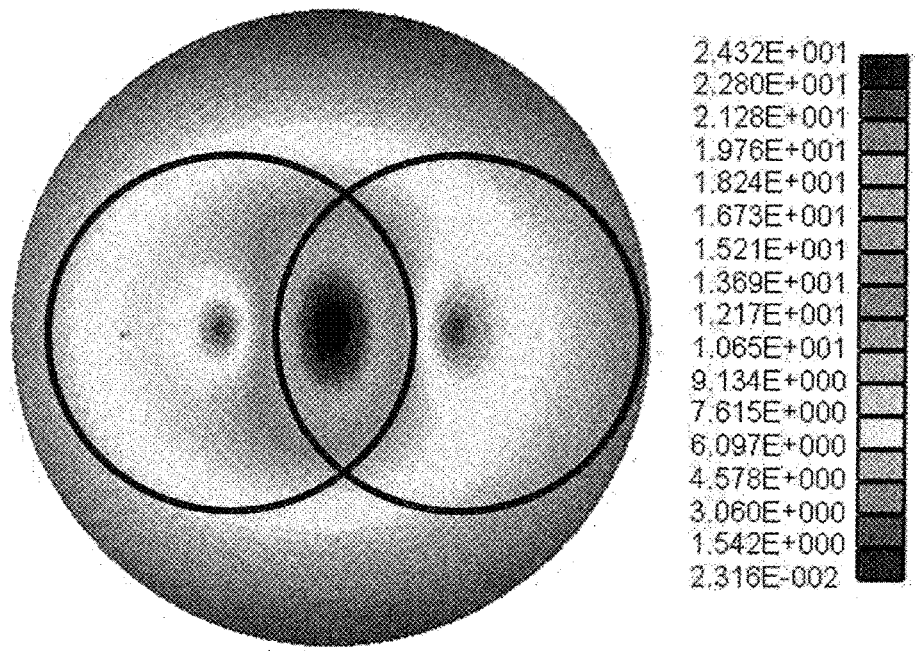
FIG. 13 is a diagram of an eddy current distribution of the figure-eight coil.
Figure 14:
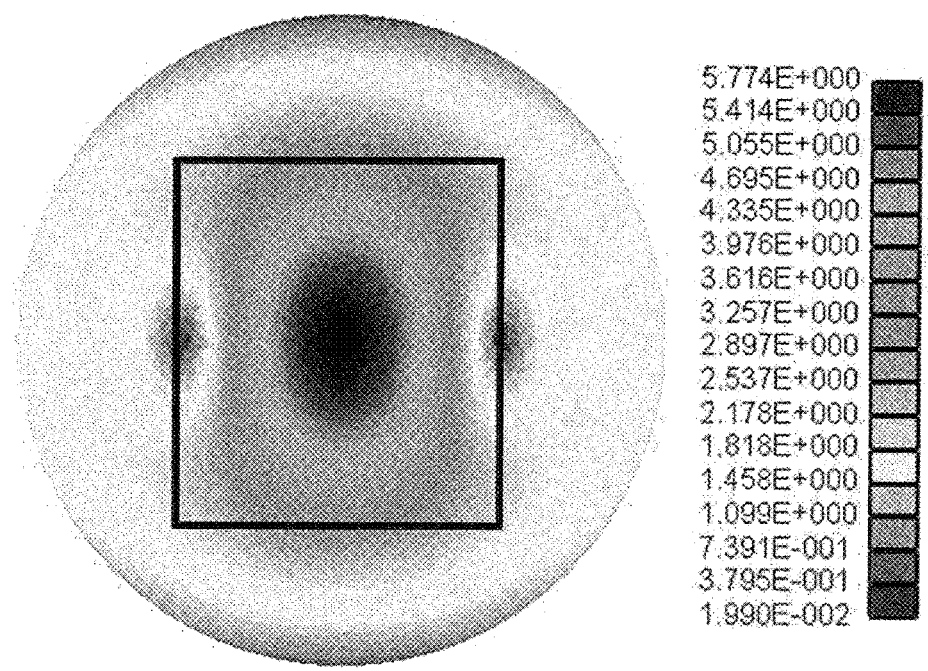
FIG. 14 is a diagram of an eddy current distribution of a reference parameter coil.
Figure 15:
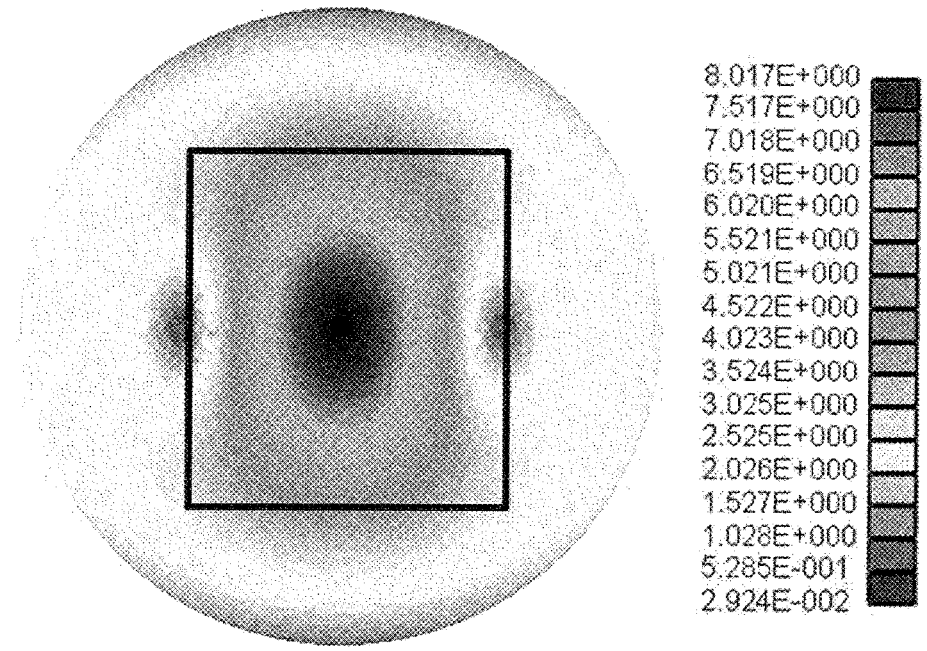
FIG. 15 is a diagram of an eddy current distribution of a most effective coil.

Embodiments of a transcranial magnetic stimulation system and a coil device used therein according to the present invention will now be described with reference to the accompanying drawings.

Although terms meaning certain directions (e.g., "upper", "lower", "left", and "right") and other terms including the terms are used in the following description, these terms are used for facilitating the understanding of the present invention with reference to the drawings, and the present invention should not be construed in a limited manner due to the meanings of these terms. In a plurality of embodiments described below, the same or similar constituent portions are denoted by the same reference numerals.

First Embodiment

Figure 22:
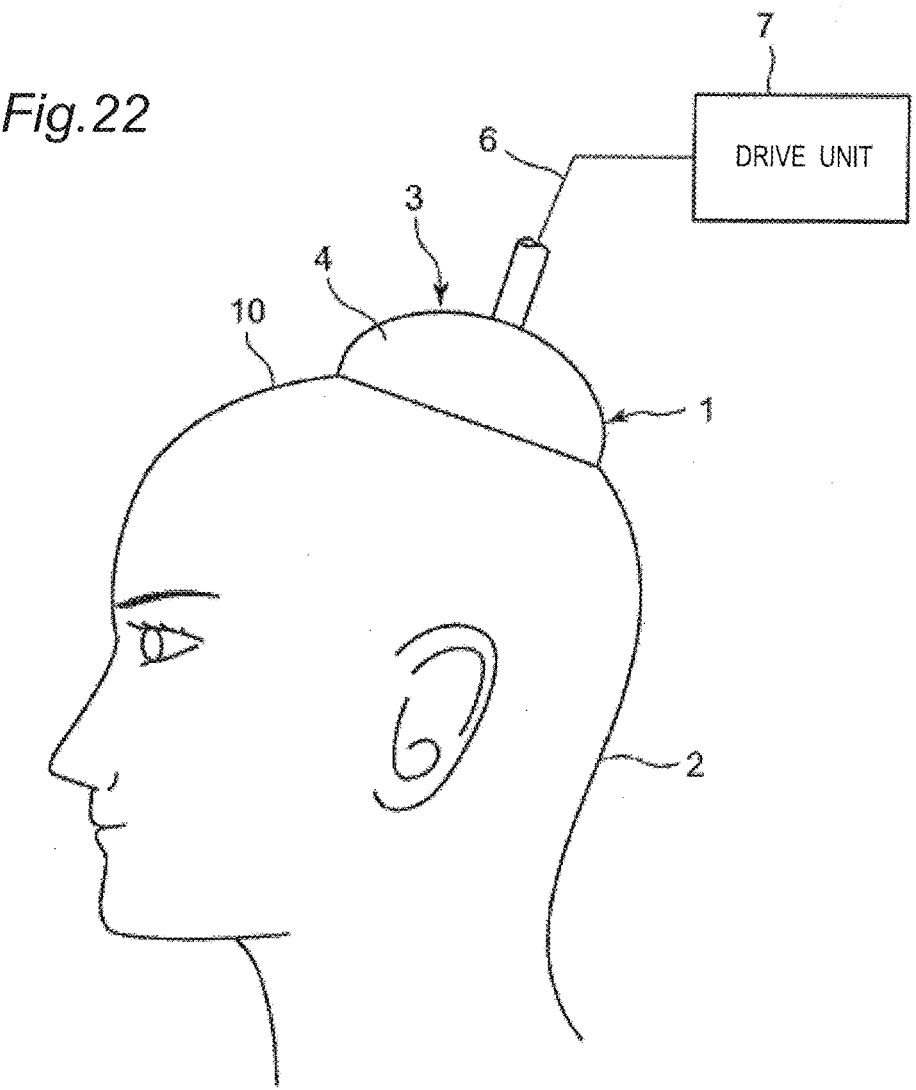
FIG. 22 is a diagram of a transcranial magnetic stimulation system according to the present invention.

Referring to FIG. 22, a transcranial magnetic stimulation system (hereinafter simply referred to as a "system") 1 has a magnetic stimulation device 3 applying a magnetic stimulation to the brain of a patient 2 supported by a support mechanism not shown (e.g., a chair, a bed).

The magnetic stimulation device 3 has a coil unit (coil device) 4 forming a dynamic magnetic field for applying the magnetic stimulation to a certain site of the brain of the patient 2. As shown, the coil unit 4 is preferably supported by a proper supporting unit (not shown) to enable movement along a head surface of the patient 2 and positioning at an arbitrary position.

Figure 24:
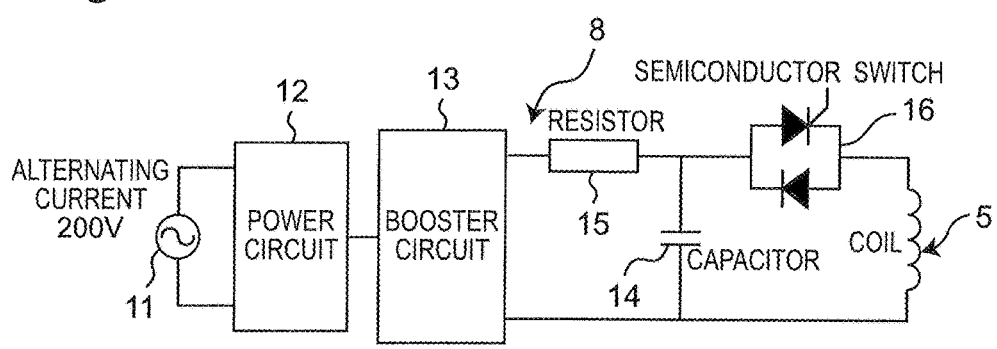
FIG. 24 is a diagram of a drive circuit of the system shown in FIG. 22.
Figure 25A:
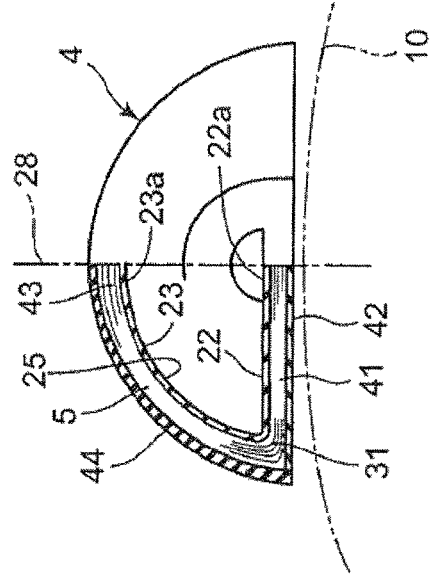
FIG. 25A is a longitudinal cross-sectional view of a coil unit shown in FIG. 22.
Figure 25C:
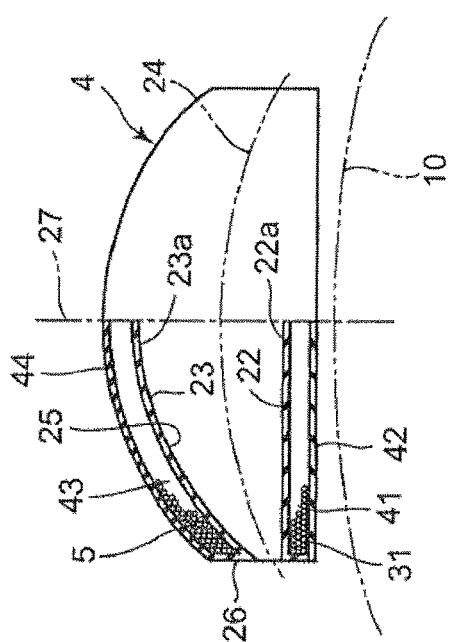
FIG. 25C is a partially cutaway plan view of a coil unit shown in FIG. 22.
Figure 25B:
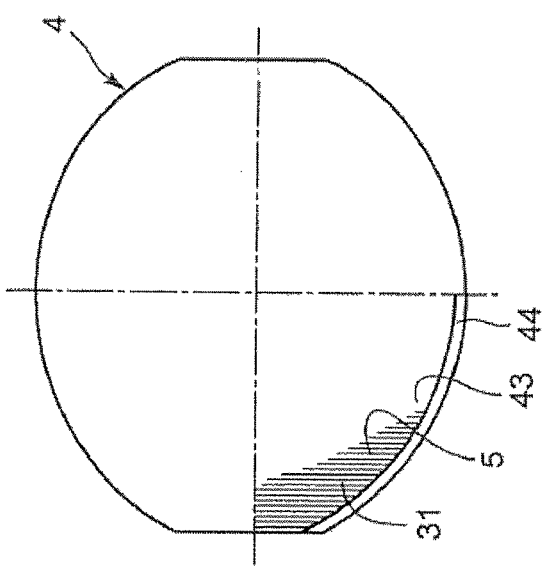
FIG. 25B is a transverse cross-sectional view of the coil unit shown in FIG. 22.

The coil unit 4 includes a coil 5 (see FIGS. 25A-25C). The coil 5 is connected through a cable 6 to a drive unit 7. The drive unit 7 includes a drive circuit 8 (see FIG. 24) described later, and the coil 5 is connected to the drive circuit 8.

As shown in FIG. 24, the drive circuit 8 has a power circuit 12 converting an output voltage of a power source 11 into a desired voltage, a booster circuit 13 boosting an output of the power circuit 12, a capacitor 14 storing an electric charge by utilizing an output from the booster circuit 13, a resistor 15 adjusting a current flowing through the capacitor 14, and a semiconductor switch 16 operating at predetermined timing for the output from the capacitor 14 to form a predetermined current, and the current adjusted by the semiconductor switch 16 is applied to the coil 5. It should be understood that in the present invention, the current applied to the coil includes not only a current having a flow direction periodically changing over time (alternating current) but also a current having a constant flow direction and a periodically varying magnitude (so-called "pulsating current").

As shown in detail in FIGS. 25A to 25C, the coil unit 4 has a spool 21 made of a non-magnetic electric insulating material. As shown, the spool 21 is a tubular member made up of a bottom wall 22 located close to the patient's head 10 in a usage state shown in FIG. 22 and a ceiling wall 23 located away from the patient's head 10 in the usage state and includes a neutral axis 24 extending in a horizontal direction of FIG. 25A. In an example, the bottom wall 22 has a flat plate shape. The ceiling wall 23 has a convex dome shape in a direction from the lower side toward the upper side of FIGS. 25A and 25B (in the direction away from the head). Specifically, a cross section of the ceiling wall 23 along a vertical plane including the neutral axis 24 as shown in FIG. 25A forms an upward convex curved surface, and a cross section of the ceiling wall 23 along a vertical plane orthogonal to the neutral axis 24 as shown in FIG. 25B also forms an upward convex curved surface. A tubular surface 25 acquired by connecting an outer surface portion 22a of the bottom wall 22 and an outer surface portion 23a of the ceiling wall 23 forms a conductive wire winding surface described later. The neutral axis 24 is a line acquired by connecting centroids (centers of gravity) defined on the transverse cross sections of the tubular surface 25.

Preferably, at both ends of the spool 21 (left and right end parts of FIG. 25A), the bottom wall 22 and the ceiling wall 23 include brims (flanges) 26 extending in a direction away from the neutral axis 24 (outward). The brims 26 may be continuous or may not be continuous (i.e., may be discontinuous) around the neutral axis 24.

The spool 21 having such a configuration is preferably formed by combining, for example, two divided pieces divided along imaginary lines 27, 28 shown in FIGS. 25A and 25B, or two divided pieces divided along a coupling part between the bottom wall 22 and the ceiling wall 23, or three or more divided pieces divided by proper cross sections.

The coil 5 is formed by winding a conductive wire 31 on the conductive wire winding surface of the spool 21 (the outer circumferential surfaces of the bottom wall 22 and the ceiling wall 23) around the neutral axis 24. As shown, the transverse cross section of the coil 5 (the transverse cross section orthogonal to the neutral axis) is small on the both end sides of the spool 21 and has a maximum size at the center part. Therefore, when a current is applied to the coil 5, the magnetic field formed inside the coil 5 converges from the center part toward the end parts, and the converged magnetic field is emitted toward an extended line of the neutral axis 24, i.e., toward the patient's head in the usage state.

The periphery of the coil 5 is covered with a non-magnetic electric insulating material. Specifically, as shown in FIGS. 25A and 25B, a bottom coil portion 41 disposed on the bottom wall 22 is covered with a bottom housing portion 42, and a ceiling coil portion 43 disposed on the ceiling wall 23 is covered with a ceiling housing portion 44. The bottom housing portion 42 and the ceiling housing portion 44 may not be made of the same material and may be made of different materials. In this case, for example, the bottom housing portion 42 may be formed of a thin flexible insulating sheet. The ceiling housing portion 44 is preferably made of a rigid material. The bottom housing portion 42 and the ceiling housing portion 44 may be formed by, for example, integrally molding a resin around the coil 5, or the bottom housing portion 42 and the ceiling housing portion 44 may separately be formed and assembled around the coil 5.

Figure 23:
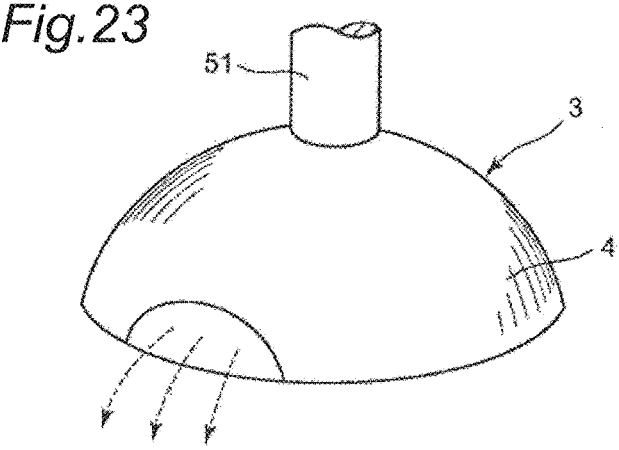
FIG. 23 is a diagram of a magnetic stimulation device of the system shown in FIG. 22.

As shown in FIG. 23, the ceiling housing portion 44 is preferably provided with a handle 51 for allowing an operator (not shown) to hold and move the coil unit 4 with a hand. In this case, the handle 51 can be made up of a hollow member with the cable 6 disposed therein.

According to the transcranial magnetic stimulation system 1 configured as described above, the bottom surface (the bottom housing portion 42) of the coil unit 4 is disposed at a proper place on the patient's head surface when used. In this state, a predetermined alternating current or pulsating current is applied from the drive circuit 8 of the drive unit 7 to the coil 5. As a result, a periodically varying magnetic field is formed inside the coil 5. This magnetic field is formed along the neutral axis 24 of the spool 21 and deflected from the center of the spool 21 toward the end parts of the spool 21 to come gradually closer to the patient's head in accordance with the shape of the spool 21, and the magnetic field emitted from the end parts of the coil 5 advances toward the patient's head. As a result, the eddy current is uniformly induced in a wide range in the patient's head. Therefore, even when the position of the coil device somewhat deviates from an intended position, the eddy current can certainly be generated in the target site.

Second Embodiment

Figure 26B:
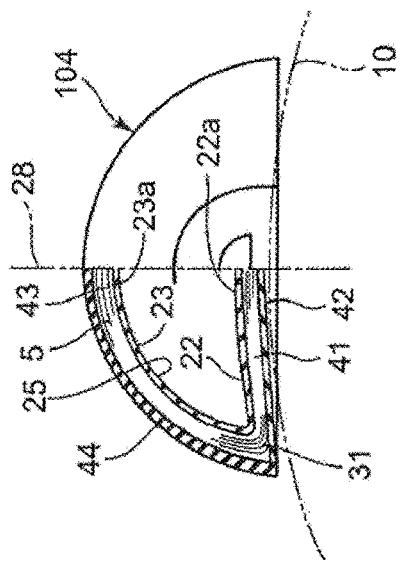
FIG. 26B is a transverse cross-sectional view of the coil unit of the second embodiment.
Figure 26A:
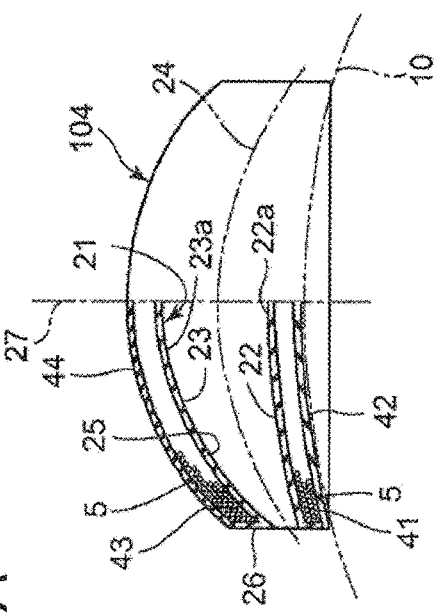
FIG. 26A is a longitudinal cross-sectional view of a coil unit of a second embodiment.
Figure 26C:
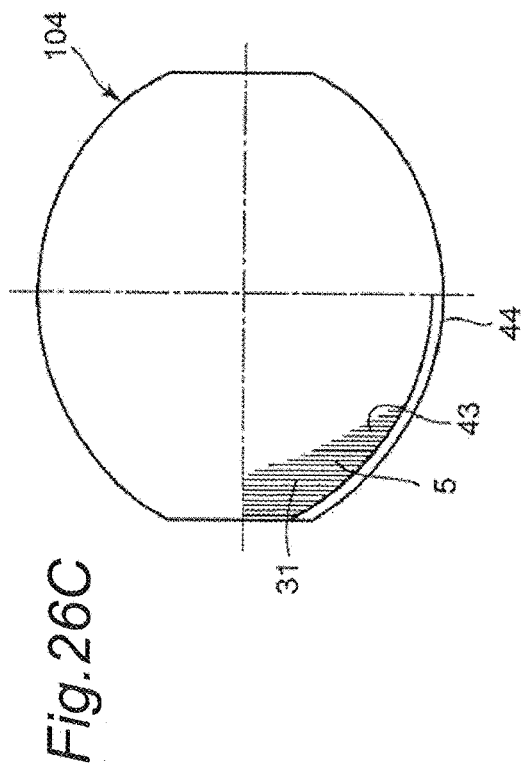
FIG. 26C is a partially cutaway plan view of the coil unit of the second embodiment.

FIGS. 26A to 26C show a coil unit 104 of a second embodiment. In this coil unit 104, the bottom wall 22 of the spool 21, particularly, the outer surface portion 22 of the bottom wall 22 (a spool outer surface) contacting with the coil 5 is recessed in a concave shape in the direction from the lower side toward the upper side of the figures (in the direction away from the head) as is the case with the ceiling wall 23 of the spool 21. Specifically, the cross sections of the bottom wall along the vertical plane including the neutral axis 24 and the vertical plane orthogonal thereto form curved surfaces recessed upward in a concave shape. The curvature of the outer surface portion 22 is obviously smaller than the curvature of the outer surface portion 23a of the ceiling wall 23 (the spool outer surface). The coil 5 is disposed in a curved shape in accordance with the curved bottom wall 22 and is covered on the outer side with the curved bottom housing portion 42. The curvature of the curved surfaces, particularly, the curvature of the bottom housing portion 42 on the outermost layer preferably substantially matches the head shape on which the coil unit 104 is placed. The other constituent elements are the same as those of the first embodiment described above.

According to the coil unit 104 of the second embodiment configured as described above, the coil unit 104 can be disposed substantially exactly along the patient's head surface and, therefore, the positioning accuracy of the coil unit 104 is further improved. Since the curvature of the neutral axis is made larger as compared to the first embodiment, a larger amount of the magnetic field can be collected inside the patient's head for more effective treatment.

Third Embodiment

FIGS. 27A and 27B show a coil unit 204 of a third embodiment. In this coil unit 204, an outer surface of the bottom housing portion 42 (a surface facing the patient's head) is recessed in a concave shape in the direction from the lower side toward the upper side of the figures (in the direction away from the head). Specifically, a bottom surface of the bottom housing portion 42 along the vertical plane including the neutral axis 24 and the vertical plane orthogonal thereto forms a curved surface recessed upward in a convex shape. The curvature of the curved surfaces, particularly, the curvature of the bottom housing portion 42 on the outermost layer preferably substantially matches the head shape on which the coil unit 104 is placed. The other constituent elements are the same as those of the first embodiment described above.

According to the coil unit 204 of the second embodiment configured as described above, the coil unit 204 can be disposed substantially exactly along the patient's head surface and, therefore, the positioning accuracy of the coil unit 204 is further improved.

Although the spool is a hollow tubular member in the above embodiments, the spool may be a solid tubular member without a space between the bottom wall and the ceiling wall.

Fourth Embodiment

Figure 28A:
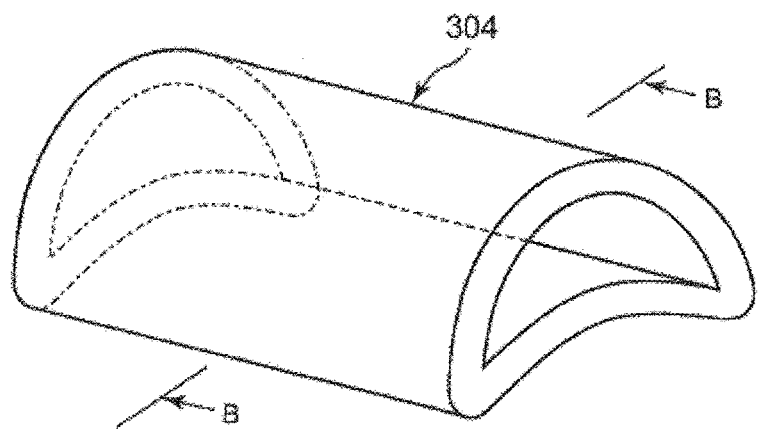
FIG. 28A is a perspective view of a coil device in another form of the present invention.
Figure 28B:
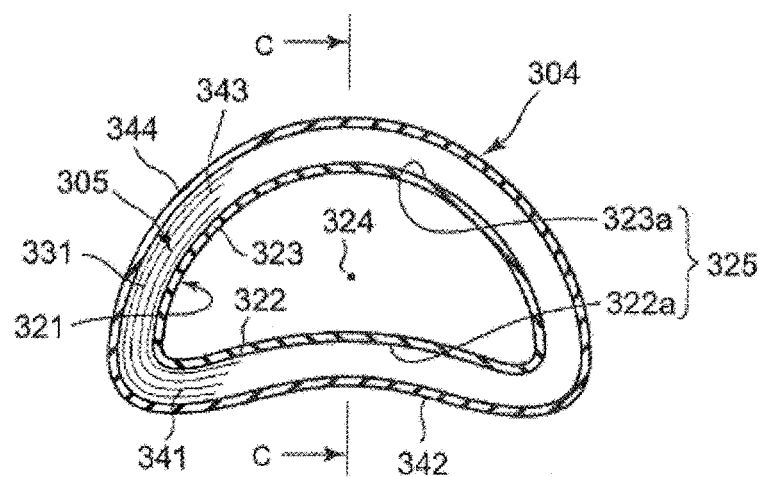
FIG. 28B is a transverse cross-sectional view of the coil device in another form of the present invention.
Figure 28C:
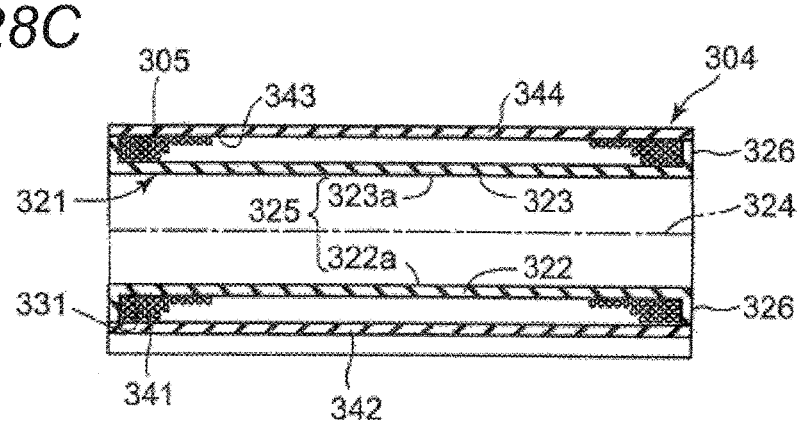
FIG. 28C is a longitudinal cross-sectional view of the coil device in another form of the present invention.

FIGS. 28A to 28C show a coil unit 304 with a crescent-shaped cross section according to a fourth embodiment. As shown, the coil unit 304 has a spool 321 with a substantially crescent-shaped transverse cross section made of a non-magnetic electric insulating material. As shown, the spool 321 is a tubular member made up of a bottom wall 322 located close to the patient's head 10 in the usage state and a ceiling wall 323 located away from the patient's head 10 in the usage state and includes a neutral axis 324 extending in a horizontal direction of FIG. 28B. In an example, the bottom wall 322 has a curved surface recessed in a concave shape in the direction from the lower side toward the upper side of FIG. 28B (in the direction away from the head). The ceiling wall 23 has a curved surface in a convex shape in a direction from the lower side toward the upper side of FIG. 28B (in the direction away from the head). Specifically, as shown in FIGS. 28A and 28B, the cross sections of both the bottom wall 322 and the ceiling wall 323 form upward convex curved surfaces on the vertical plane orthogonal to the neutral axis 324. Left and right connecting parts between the bottom wall 322 and the ceiling wall 323 form smooth curves. A tubular surface 325 with a substantially crescent-shaped transverse cross section acquired by connecting an outer surface portion 322a of the bottom wall 322 and an outer surface portion 323a of the ceiling wall 323 forms a conductive wire winding surface described later. The neutral axis 324 is a line acquired by connecting centroids (centers of gravity) defined on the transverse cross sections of the tubular surface 25.

Preferably, at both ends of the spool 321 (left and right end parts of FIG. 28C), the bottom wall 322 and the ceiling wall 323 include brims (flanges) 326 extending in a direction away from the neutral axis 324 (outward). The brims 326 may be continuous or may not be continuous (i.e., may be discontinuous) around the neutral axis 24.

The spool 321 having such a configuration is preferably formed by combining, for example, a plurality of divided pieces divided along a transverse cross section including the neutral axis 324 or a plurality of divided pieces divided along a transverse cross section orthogonal to the neutral axis 324.

A coil 305 is formed by winding a conductive wire 331 on a conductive wire winding surface 325 of the spool 321 (the outer surface portion 322a of the bottom wall 322 and the outer surface portion 323a of the ceiling wall 323) around the neutral axis 324. The periphery of the coil 305 is covered with a non-magnetic electric insulating material. Specifically, as shown in FIGS. 25B and 25C, a bottom coil portion 341 disposed on the bottom wall 322 is covered with a bottom housing portion 342, and a ceiling coil portion 343 disposed on the ceiling wall 323 is covered with a ceiling housing portion 344. The bottom housing portion 342 and the ceiling housing portion 344 may not be made of the same material and may be made of different materials. For example, the bottom housing portion 342 may be formed of a thin flexible insulating sheet. The ceiling housing portion 344 is preferably made of a rigid material. The bottom housing portion 342 and the ceiling housing portion 344 may be formed by, for example, integrally molding a resin around the coil 305, or the bottom housing portion 342 and the ceiling housing portion 344 may separately be formed and assembled around the coil 305. Although not shown, the ceiling housing portion 344 is preferably provided with a handle for allowing an operator (not shown) to hold and move the coil unit 304 with a hand.

According to the coil unit 304 and a transcranial magnetic stimulation system including the coil unit 304 according to the fourth embodiment, the bottom surface (the bottom housing portion 342) of the coil unit 304 is disposed at a proper place on the patient's head surface when used. In this state, a predetermined alternating current or pulsating current is applied from the drive circuit 8 of the drive unit 7 to the coil 305. As a result, a periodically varying magnetic field is formed inside the coil 305. This magnetic field is formed along the neutral axis 324 of the spool 321. The magnetic field emitted from the coil 305 advances toward the patient's head and uniformly generates the eddy current in a wide range in the patient's head. Therefore, even when the position of the coil device somewhat deviates from an intended position, the eddy current can certainly be generated in the target site. Additionally, the coil unit 304 can be disposed substantially exactly along the patient's head surface and, therefore, the positioning accuracy of the coil unit 104 is further improved.

Although the coil device of the fourth embodiment is shown such that the spool 321 has the neutral axis 324 forming a straight line, the spool 321 may be configured to have the neutral axis forming an upward convex curve. In this case, since the outer shape of the bottom housing portion can be configured to have a longitudinal center part forming an upward convex curve, the bottom surface of the bottom housing can be disposed substantially exactly along the patient's head surface.

The coil device of the fourth embodiment is configured such that the bottom wall 322 of the spool 321 has a center part in the width direction forming an upward convex curve; however, as is the case with the third embodiment, while a transverse cross section of the bottom wall 322 is formed into a straight shape to dispose a coil linearly along the bottom part 322, a bottom surface of a bottom housing may have a center part in the width direction formed into an upward convex shape (i.e., the center part in the width direction may thinly be formed and the both sides may thickly be formed), so that the bottom surface of the bottom housing is disposed substantially exactly along the patient's head surface. Also in this example, the outer shape of the bottom housing portion may be configured to have a longitudinal center part forming an upward convex curved surface.

The dimensions of the parts of the coil device according to the first to fourth embodiments described above are determined depending on specifications required for the coil device. For example, as described with reference to FIGS. 9 to 12, (a) the length of the coil in the neutral axis direction affects the eddy current spread; (b) the height of the coil affects the eddy current density; (c) the curvature (radius) of the ceiling coil portion affects the inductance; (d) the length of the coil in the width direction orthogonal to the neutral axis affects the eddy current density; and (e) the number of turns of the coil affects the eddy current density. Therefore, when the coil device is actually designed, preferably, these factors (a) to (e) are taken into consideration.

Fifth Embodiment

Description will be made of studies conducted by the present inventors for optimizing the design parameters related to a coil shape so that coil specifications satisfy various necessary conditions in the dome-type coil of the present invention, and the results thereof.

In the following studies, the following design parameters etc. are fixed in the conducted studies.

In particular, the coil is formed by winding a conductive wire having a rectangular cross section of 6×2 mm, and the number of turns of the coil is 20. The conductive wire is wound into a shape coming into contact with the scalp having the radius of 100 mm.

As described in the above embodiments, it is appropriate to use three parameters of A: coil width, B: coil height, and C: upper conductive wire radius (outer curvature) of the coil (FIG. 29A) for design parameters to be studied for acquiring the optimum design values of the dome-type coil, and these three parameters are independent of each other. From the determined coil width A, intervals between the conductive wires on the side contacting with the scalp are determined.

Figure 16:
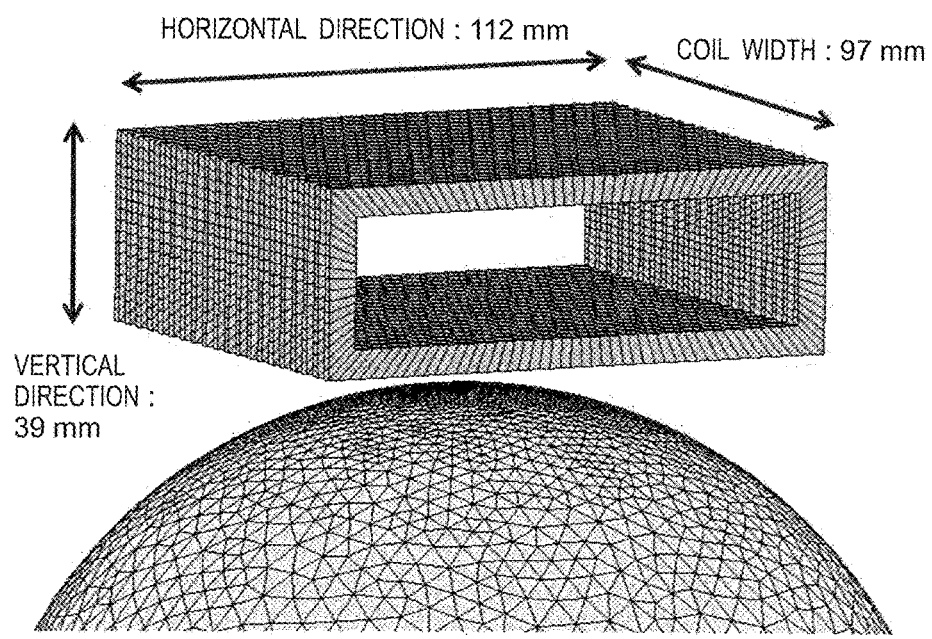
FIG. 16 is a diagram of a most effective coil model.
Figure 19:
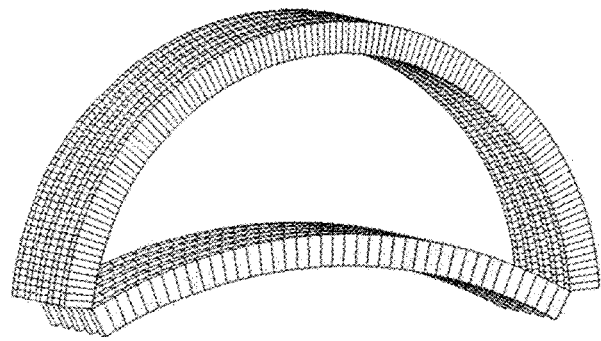
FIG. 19 is a diagram of a coil model without connection between upper and lower circular arcs.
Figure 20:
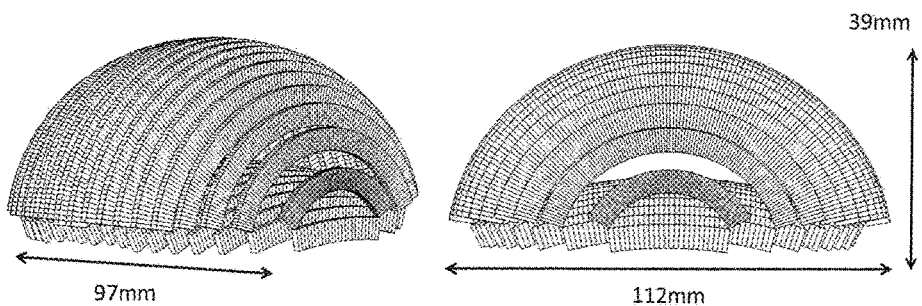
FIG. 20 is a diagram of a dome-type coil model produced based on the simplified model.
Figure 21:
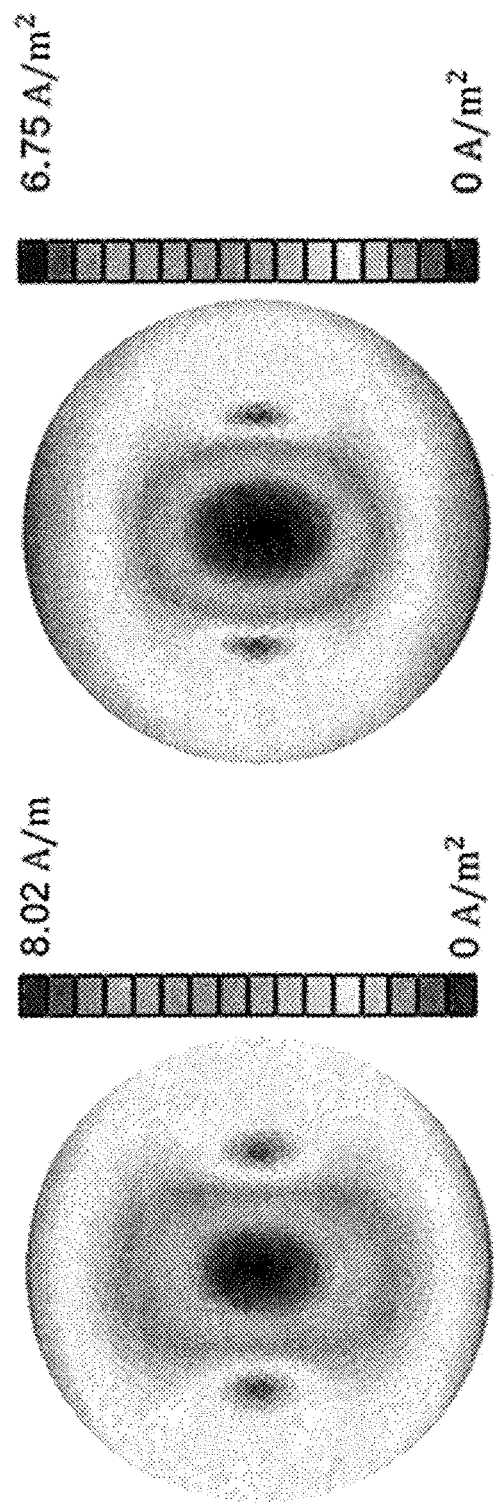
FIGS. 21A and 21B are diagrams of eddy current distributions of the coil of the simplified model and the dome-type coil viewed from the coil side.

In this embodiment, an object was to examine the tendencies of variations and the numerical ranges of variations in various characteristics when the parameter values were separately changed by using as start data one optimum solution acquired from the studies using a rectangular parallelepiped model that is the simplified dome-type coil described above, i.e., A: the coil width=97 mm, B: the coil height=39 mm, C: the upper conductive wire radius=56 mm (corresponding to the horizontal direction: 112 mm in the rectangular parallelepiped model shown in FIG. 16), so as to find out directions of design optimization and to finally acquire one of the optimized design values for the dome-type coil.

Figure 29B:
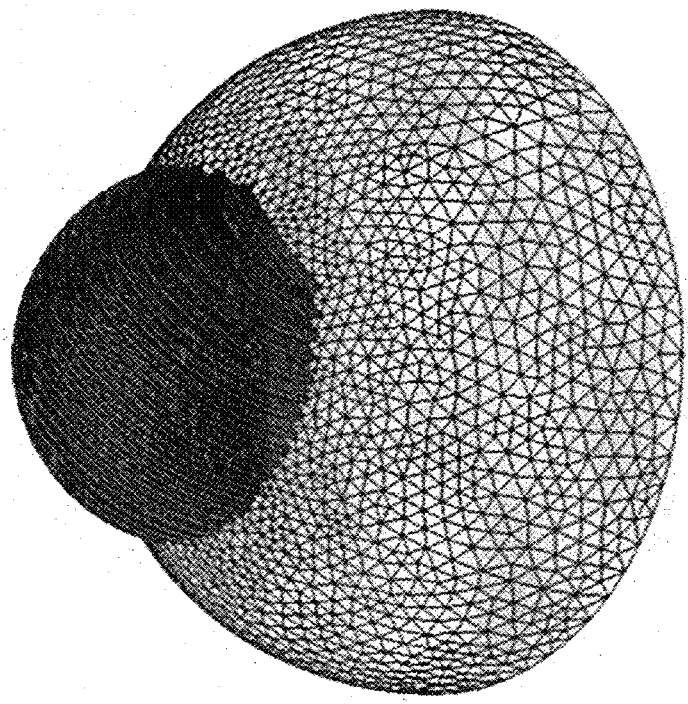
FIG. 29B is a diagram for explaining a brain model that is a spherical conductor for evaluating various characteristics of the dome-type coil of the present invention.
Figure 29A:
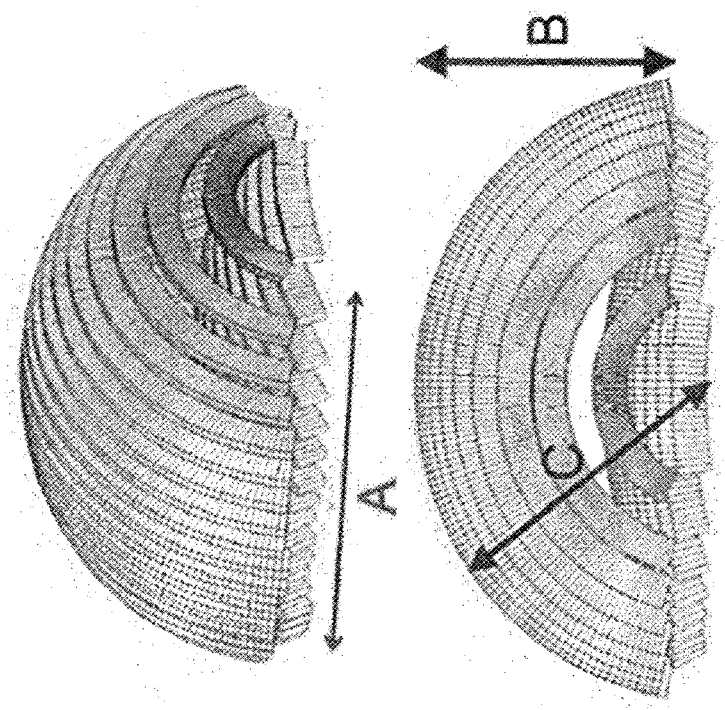
FIG. 29A is a diagram for explaining design parameters that are objects of optimized design of the dome-type coil of the present invention.

To evaluate the characteristics of the dome-type coil and the distribution of the induced electric field, the present inventors uniquely developed numerical models of the coil and the brain. In particular, as shown in FIG. 29B, the brain was modeled as a spherical-shaped (spherical) conductor having the diameter of 200 mm. The electric conductivity of this brain model was set to 0.11 S/m from the electric conductivity of the grey matter at 3.4 kHz (S. Gabriel, R. W. Lau, and C. Gabriel, Phys. Med. Biol. 41, 2231 (1996)). The coil model was disposed 10 mm above the brain model, and this interval was defined in accordance with the thickness of the scalp and the skull. This analysis was performed by using "PHOTO-Series for Windows (registered trademark) manufactured by PHOTON," which is a commercially available computer program based on the finite element method (M. Sekino and S. Ueno, IEEE Trans. Magn. 40, 2167 (2004)). The alternating current applied to the coil was set to the frequency of 3.4 kHz and the current value of 5.3 kA, and this is a typical alternating pulse width of a TMS device using a wavelength band of 200 to 300 µs.

Figure 30:
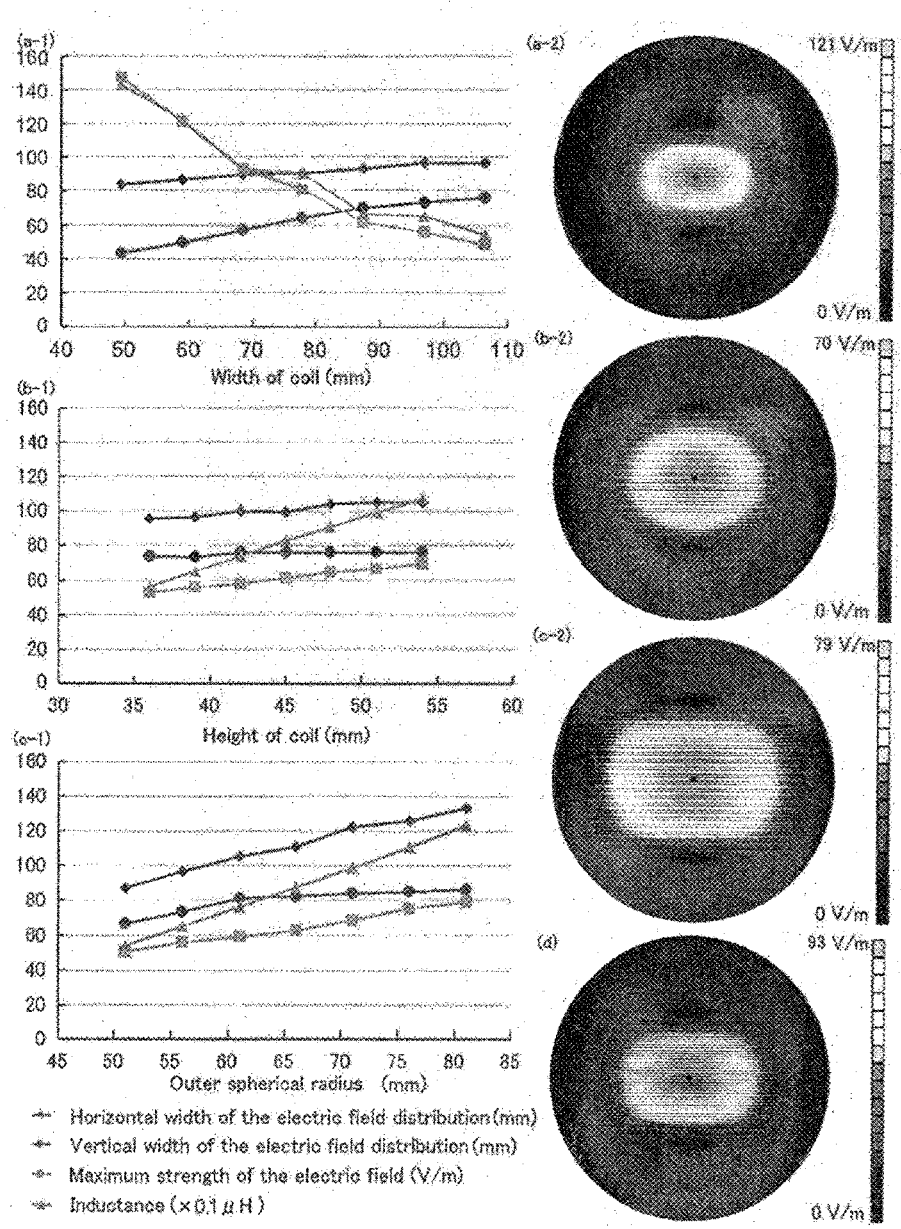
FIG. 30 is a diagram of various characteristic values of the coil and induced electric field intensity distributions when the design parameters are changed in the dome-type coil of the present invention.

According to the numerical simulation described above in the embodiments, what design parameter is selected in the dome-type coil affects the coil characteristics and the electric field distribution. As shown in FIG. 30($a$-1), when the coil width A is increased, the maximum intensity of the induced electric field and the inductance of the coil are reduced, while the range of distribution of the induced electric field is expanded. This reveals that, to increase the electric field intensity, the coil width A may be made smaller. However, since an excitation pulse width increases unless the inductance of the coil is made smaller than 12.6 µH, the electric field intensity must be made smaller than 121 V/m. Under this condition, the range of distribution of the induced electric field is narrowed to 86×50 mm.

As shown in FIG. 30($b$-1), when the coil height B is increased, the inductance of the coil increases. The distribution range of the induced electric field slightly widens, and the intensity of the induced electric field also slightly increases. If it is attempted to increase the induced electric field intensity in this way, the electric field intensity and the electric field distribution range reach limits at 70 V/m and 105×76 mm, respectively. These limits are determined by the upper conductive wire radius (outer curvature) C rather than the inductance condition of the coil. In particular, this is because the upper conductive wire radius C is set to 56 mm and the coil height B must geometrically be a value smaller than 56 mm.

Additionally, as shown in FIG. 30(c-1), when the upper conductive wire radius C increases, the inductance of the coil increases, and the induced electric field distribution range also widens. If the induced electric field is increased in this way, the induced electric field intensity and the induced electric field distribution range reach limits at 79 V/m and 133×86 mm, respectively. These limits are derived from the condition that the value of the inductance of the coil must be within a necessary range.

By using a method of changing each of the three design parameters, the effectiveness of the dome-type coil can be improved. FIG. 30 and Table 4 summarize how the coil characteristics are improved when each of the design parameters is changed. The best way to increase the induced electric field intensity and the induced electric field range is to increase the upper conductive wire radius C. However, if the upper conductive wire radius C is increased, the size of the coil itself increases. When the electric resistance of the coil is taken into consideration, an increase in the coil size results in an increase in the resistance value of the whole coil and thus results in an increase in the heat generation of the coil. Therefore, if the number of excitation pulses becomes large in rTMS (repetitive TMS: repetitive magnetic stimulation), heat generation exceeds the limit, which leads to the necessity to limit the number of excitation pulses to a certain limit or less, and thus, the method of increasing the size of the coil is not considered as a desirable method (T. Weyh, K. Wendicke, C. Mentschel, H. Zantow, and H. R. Siebner, Clin. Neurophysiol. 116, 1477 (2005)). The heat generation derived from the equation $P=I^2R$ occurs in proportion to the resistance value of the coil. Therefore, since narrowing the coil width A does not increase the heat generation although the range of the induced electric field is narrowed, this is the most effective method for increasing the induced electric field intensity among the three methods of changing the design parameters.

TABLE 4

| Study step | Start data | Change in coil width (59 mm) | Change in coil height (54 mm) | Change in upper conductive wire radius (81 mm) | Optimized design |
|---|---|---|---|---|---|
| A: coil width [mm] | 97 | 59 | 97 | 97 | 78 |
| B: coil height [mm] | 39 | 39 | 54 | 39 | 39 |
| C: upper conductive wire radius [mm] | 56 | 56 | 56 | 81 | 66 |
| Induced electric field maximum value [V/m] | 56 | 121 | 70 | 79 | 93 |
| Half-value width of electric field maximum value [mm] | 97 × 73 | 86 × 50 | 105 × 76 | 133 × 86 | 106 × 68 |
| Coil Inductance [μH] | 6.5 | 12.2 | 10.7 | 12.3 | 11.4 |

It is considered that the optimum method for improving the coil effectiveness and the robustness against position deviation is to perform two methods, i.e., narrowing the coil width A and increasing the upper conductive wire radius C, at the same time. Based on the results described above, the present inventors were able to attain a model having the coil width of 78 mm, the coil height of 39 mm, and the upper conductive wire radius of 66 mm as the dome-type coil with the optimized design. FIG. 30(d) shows the induced electric field intensity distribution of the model acquired as a result. The model has the induced electric field intensity maximum value of 93 V/m, the induced electric field distribution of 106×68 mm, and the coil inductance of 11 μH. Comparing to the start mode described earlier, it can be seen that the optimized modes describe above is improved in the induced electric field intensity without widening of the induced electric field distribution.

For the optimized design model acquired this time, i.e., the model having the coil width of 78 mm, the coil height of 39 mm, and the coil upper conductive wire radius of 66 mm, the design values can be selected from different values as needed within ranges in which the selected design values produce substantially the same effects as described above. Specifically, any or all of the coil width of 78 mm, the coil height of 39 mm, and the upper conductive wire radius of 66 mm are increased or reduced within a range of 10% in such a model.

The present inventors further performed analyses of the respective dome-type coils of the start data model described earlier and the optimized model by using a self-produced computer program based on the SPFD method (the scalar-potential finite-difference method: scalar-potential finite element method), in a numerical brain model (realistic brain model) (T. Nagaoka, S. Watanabe, K. Sakurai, E. Kunieda, S. Watanabe, M. Taki, and Y. Yamanaka, Phys. Med. Biol. 49, 1 (2004)). The results thereof are shown in FIGS. 31A and 31B. The 99.9th percentile value of all the voxels was 55 V/m in the coil of the start data model (FIG. 31A) and 83 V/m in the coil of the optimized model (FIG. 31B), and the effectiveness of this model was able to be confirmed not only in the simple spherical model but also in the analysis under the conditions closer to the actual brain.

EXPLANATIONS OF LETTERS OR NUMERALS

1 transcranial magnetic stimulation system
2 patient
3 magnetic stimulation device
4 coil unit (coil device)
5 coil 6 cable
7 drive unit
8 drive circuit
10 patient's head
11 power source
12 power circuit
13 booster circuit
14 capacitor
15 resistor
16 semiconductor switch
21 spool
22 bottom wall
22a bottom wall outer surface portion
23 ceiling wall
23a ceiling wall outer surface portion
24 neutral axis
25 tubular surface
26 brim
27, 28 imaginary line
31 conductive wire
32
41 bottom coil portion
42 bottom housing portion
43 ceiling coil portion
44 ceiling housing portion
A coil width
B coil height
C coil upper conductive wire radius

The invention claimed is:

1. A coil device used in a transcranial magnetic stimulation treatment that is configured to be placed on or near a head surface to stimulate neurons by inducing an eddy current in the brain through electromagnetic induction, the coil device comprising:
   a spool having a neutral axis acquired by connecting centers of gravity in transverse cross sections and a tubular surface surrounding the neutral axis; and
   a coil made up of a conductive wire wound on the tubular surface around the neutral axis,
   the tubular surface having
   an inner surface portion configured to be located close to the head surface during use, and
   an outer surface portion forming a convex curved surface protruding outward of the tubular surface with respect to a first direction parallel to the neutral axis and a second direction orthogonal to the first direction,
   the coil having end-part transverse cross sections on one end side and an other end side of the neutral axis smaller than a center-part transverse cross section located at a center between the one end side and the other end side,
   the neutral axis forming a convex curve protruding from the inner surface portion toward the outer surface portion.

2. The coil device according to claim 1, wherein the inner surface portion is a curved surface recessed in a concave shape toward an inside of the tubular surface.

3. The coil device according to claim 1, wherein the inner surface portion is a flat surface.

4. The coil device according to claim 1, wherein the coil device has an outer housing portion covering a coil portion located on the outer surface portion.

5. The coil device according to claim 1, wherein the coil device has an inner housing portion covering a coil portion located on the inner surface portion.

6. The coil device according to claim 5, wherein the inner housing portion has an outer surface that is a curved surface recessed in a concave shape toward an inside of the tubular surface.

7. The coil device according to claim 1, wherein the tubular surface has end-part transverse cross sections on one end side and an other end side of the neutral axis smaller than a center-part transverse cross section located at a center between the one end side and the other end side.

8. The coil device according to claim 7, wherein the transverse cross sections of the tubular surface are configured to become gradually smaller from the center-part transverse cross section toward the end-part transverse cross sections.

9. The coil device according to claim 1, wherein the neutral axis is an axis passing through centroids or centers of gravity of transverse cross sections of the tubular surface.

10. The coil device according to claim 1, wherein the spool is made up of a hollow member extending along the neutral axis.

11. The coil device according to claim 1, wherein the spool is made up of a solid member.

12. A coil device used in a transcranial magnetic stimulation treatment that is configured to be placed on or near a head surface to stimulate neurons by inducing an eddy current in the brain through electromagnetic induction, the coil device comprising:
    a spool having a neutral axis acquired by connecting centers of gravity in transverse cross sections and a tubular surface surrounding the neutral axis; and
    a coil made up of a conductive wire wound on the tubular surface around the neutral axis,
    the coil having end-part transverse cross sections on one end side and an other end side of the neutral axis smaller than a center-part transverse cross section located at a center between the one end side and the other end side,
    the tubular surface having an inner surface portion configured to be located close to the head surface during use and an outer surface portion configured to be located away from the head surface during use, both the inner surface portion and the outer surface portion forming convex curved surfaces protruding outward.

13. A transcranial magnetic stimulation system comprising: the coil device according to claim 1.

* * * * *